United States Patent
De Vries et al.

(10) Patent No.: US 10,925,944 B2
(45) Date of Patent: Feb. 23, 2021

(54) CELL POPULATION FOR USE IN TREATING CANCER

(71) Applicant: MILTENYI BIOTEC B.V. & CO. KG, Bergisch Gladbach (DE)

(72) Inventors: Jolanda De Vries, Nijmegen (NL); Carl Figdor, Nijmegen (NL); Ghaith Bakdash, Nijmegen (NL)

(73) Assignee: MILTENYI BIOTEC B.V. & CO. KG, Bergisch Gladbach (DE)

( * ) Notice: Subject to any disclaimer, the term of this patent is extended or adjusted under 35 U.S.C. 154(b) by 232 days.

(21) Appl. No.: 15/510,222

(22) PCT Filed: Sep. 10, 2015

(86) PCT No.: PCT/EP2015/070778
§ 371 (c)(1),
(2) Date: Mar. 9, 2017

(87) PCT Pub. No.: WO2016/038168
PCT Pub. Date: Mar. 17, 2016

(65) Prior Publication Data
US 2017/0258882 A1     Sep. 14, 2017

(30) Foreign Application Priority Data

Sep. 10, 2014  (EP) ..................................... 14184333
Sep. 10, 2014  (EP) ..................................... 14184334
Sep. 12, 2014  (EP) ..................................... 14184687

(51) Int. Cl.
*A61K 35/15*     (2015.01)
*A61K 39/00*     (2006.01)
*C12N 5/0784*    (2010.01)
*A61K 35/12*     (2015.01)

(52) U.S. Cl.
CPC .......... *A61K 39/0011* (2013.01); *A61K 35/15* (2013.01); *C12N 5/0639* (2013.01); *A61K 2035/124* (2013.01); *A61K 2039/5154* (2013.01); *A61K 2039/57* (2013.01); *A61K 2039/585* (2013.01)

(58) Field of Classification Search
CPC ... A61K 39/0011; A61K 35/15; C12N 5/0639
USPC ..................................................... 424/278.1
See application file for complete search history.

(56) References Cited

U.S. PATENT DOCUMENTS 5,849,589 A   12/1998   Tedder et al.
7,030,228 B1  4/2006    Schmitz et al.

FOREIGN PATENT DOCUMENTS

| JP | 2003-511064 A | 3/2003 |
|----|---------------|--------|
| JP | 2004-512006 A | 4/2004 |
| WO | 98/53048 A1   | 11/1998 |
| WO | 01/36487 A2   | 5/2001 |
| WO | 01/51617 A1   | 7/2001 |
| WO | 2004/108753 A1 | 12/2004 |

OTHER PUBLICATIONS

Cheng et al. (J Immunol., Apr. 1, 2010, 184 (1 Supplement), abstract No. 144.14, pp. 1-4).*
"FDA Approved Antibody-based Therapeutics", The Immunology Link, accessed at https://web.archive.org/web/20150815203206/http://immunologylink.com/FDA-APP-Abs.html, accessed on Mar. 1, 2017, pp. 3.
Banchereau and Steinman, "Dendritic cells and the control of immunity", Nature, vol. 392, No. 6673, 1998, pp. 245-252.
Figdor, et al., "Dendritic cell immunotherapy: mapping the way", Nature Medicine, vol. 10, No. 5, May 2004, pp. 475-480.
Gigante et al., "Dysfunctional DC subsets in RCC patients: Ex vivo correction to yield an effective anti-cancer vaccine", Molecular Immunology, vol. 46, Issue 5, Feb. 2009, pp. 893-901.
Liu, "Dendritic Cell Subsets and Lineages, and Their functions in Innate and Adaptive Immunity", Cell, vol. 106, No. 3, Aug. 2001, pp. 259-262.
Tacken, et al., "Dendritic-cell immunotherapy: from ex vivo loading to in vivo targeting", Nature Reviews Immunology, vol. 7, Oct. 2007, pp. 790-802.
Ziegler-Heitbrock, et al., "Nomenclature of monocytes and dendritic cells in blood", Blood, vol. 116, No. 16, Oct. 2010, pp. e74-e80.
Collin, et al. "Monocyte, Macrophage, and Dendritic Cell Development: the Human Perspective" Microbiology Spectrum 4: MCHD-0015-2015. doi: 10.1128/microbiolspec Jan. 12, 2017.
Thomas, et al. "Human peripheral blood dendritic cell subsets. Isolation and characterization of precursor and mature antigen-presenting cells" Journal of Immunology vol. 153, Issue 9, 4016-4028, Nov. 1, 1994.
Van Ee, et al. "BDCA1+CD14+ Immunosuppressive Cells in Cancer, a Potential Target?" Vaccines Sep. 19, 2018, 6, 65.
Ziegler-Heitbrock, et al. "Nomenclature of monocytes and dendritic cells in blood" Blood vol. 116, Issue 16, Oct. 21, 2010, https://doi.org/10.1182/blood-2010-02-258558.

\* cited by examiner

*Primary Examiner* — Yan Xiao

(74) *Attorney, Agent, or Firm* — Maschoff Brennan

(57) ABSTRACT

The invention pertains to a cell population for use in treating cancer in a patient, comprising CD1c(BDCA-1)$^+$/CD19$^-$ dendritic cells, wherein CD1c(BDCA-1)$^+$/CD19$^-$ dendritic cells are depleted for CD1c(BDCA-1)$^+$/CD19$^-$/CD14$^+$ cells.

7 Claims, 22 Drawing Sheets

R1: FcεR1⁻CD1c^low CD14^high supressor cells
R2: CD1c⁺FcεR⁺CD14^−/low MDCs

CELL POPULATION FOR USE IN TREATING CANCER

The invention pertains to a cell population comprising myeloid dendritic cells CD1c (BDCA-1)$^+$ that are loaded with a tumor antigen or a tumor peptide, in particular for use in treating cancer in a patient.

INTRODUCTION

Dendritic cells (DCs) are central players in immune responses. As professional antigen-presenting cells, DCs sample the tissue microenvironment and phagocytize both pathogen-derived products and dying host cells, including tumor cells (Banchereau J, Steinman R M. Dendritic cells and the control of immunity. Nature 1998; 392:245-252). DCs have the unique capacity to attract and activate nave (tumor) antigen-specific CD4$^+$ and CD8$^+$ T cells. DC-based immunotherapy exploits this property of DCs: Tumor-antigen-loaded DCs are injected into cancer patients to stimulate T cells and initiate tumor eradication (Figdor C G, de Vries I J M, Lesterhuis W J, Melief C J M. Dendritic cell immunotherapy: mapping the way. Nature Medicine 2004; 10:475-480; Tacken P J, de Vries I J M, Torensma R, Figdor C G. Dendritic-cell immunotherapy: from ex vivo loading to in vivo targeting. Nat. Rev. Immunol. 2007; 7:790-802).

DCs for immunotherapy are commonly prepared in vitro from monocyte precursors. The extensive culture period (8 to 9 days) and compounds required to differentiate them into DCs may negatively affect their immunological potential.

Accordingly, there is a need in the art for alternative DC-based immunotherapy approaches.

SHORT DESCRIPTION OF THE INVENTION

In one aspect, the invention refers to a cell population, in particular for use in treating cancer in a patient, comprising or consisting of CD1c+/CD19− dendritic cells, wherein less than or equal to 25% of these CD1c+/CD19− dendritic cells are CD1c+/CD19−/CD14+ cells.

Said cell population may further comprise or consist of cells that are also CD304 (BDCA-4).

In one embodiment, at least 50% of the cells are loaded with a tumor antigen or a tumor peptide.

The cells may be purified from blood, in particular from the blood of a patient in need of a cancer treatment. The cancer may be a solid cancer, such as chronic myeloid leukemia, melanoma or prostate cancer.

In another aspect, the invention refers to a kit for producing a cell population for treating cancer in a patient and its use in producing a cell population for treating cancer in a patient. Such a kit comprises or consists of the following components:
  An antibody capable of binding to CD1c (BDCA-1),
  An antibody capable of binding to a monocyte, preferably to suppressive DCs,
  An antibody capable of binding to a B cell, in particular CD19 or CD20, and, and optionally
  An antibody capable of binding to CD304 (BDCA-4).

In another aspect, the invention refers to a method for treating cancer, comprising
  Administering a cell population as described above and herein to a patient suffering from cancer.

BRIEF DESCRIPTION OF THE DRAWINGS

FIGS. 1A-1C: Graphs showing BDCA1+CD14+ DCs, which are associated with cancer, in which Figure 1A shows that the percentage of BDCA1+CD14+ cells is increased in cancer patients, FIG. 1B shows higher percentages of BDCA1+CD14+ in ovarian cancer, and FIG. 1C shows phenotyping different cell subsets.

FIGS. 4A-4D: Graphs showing BDCA1+CD14+ cells, which possess DC characteristics, in which FIG. 4A shows that BDCA1+CD14+ cells are veg efficient in antigen uptake, FIG. 4B shows that BDCA1+CD14+ cells upregulate the costimulatogy molecule CD80 upon stimulation with TLR ligands, and FIGS. 4C-4D show that BDCA1+CD14+ cells possess a unigue inflammatory cytokine profile.

FIGS. 6A-6B: Graphs showing that reduced activity of BDCA1+CD14+ cells is caused by PD-L1 and MERTK expression, in which FIG. 6A shows that BDCA1+CD14+ DCs upregulate PD-L1 in response to TLR stimulation and FIG. 6B shows that PD-L1 blocking enhances the T cell stimulatom capacity of BDCA1+CD14+.

FIGS. 7A-7D: Graphs showing that BDCA1+CD14+ cells are associated with lower response towards cancer immunotherapy in melanoma patients, in which FIG. 7A shows that higher percentages of BDCA1+CD14+ cells in myeloid DC immunotherapy correlate with lower responses in patients, FIGS. 7B-7C show that BDCA1+CD14+DCs suppress the proliferation of KLH-specific CD4+ T cells and that BDCA1+CD14+ DCs suppressor capacity is inhibited by Oxaliplatin, and FIG. 7D shows that DCA1+CD14+ DCs do not suppress polyclonal T cell proliferation.

DETAILED DESCRIPTION OF THE INVENTION

Figure 1A:
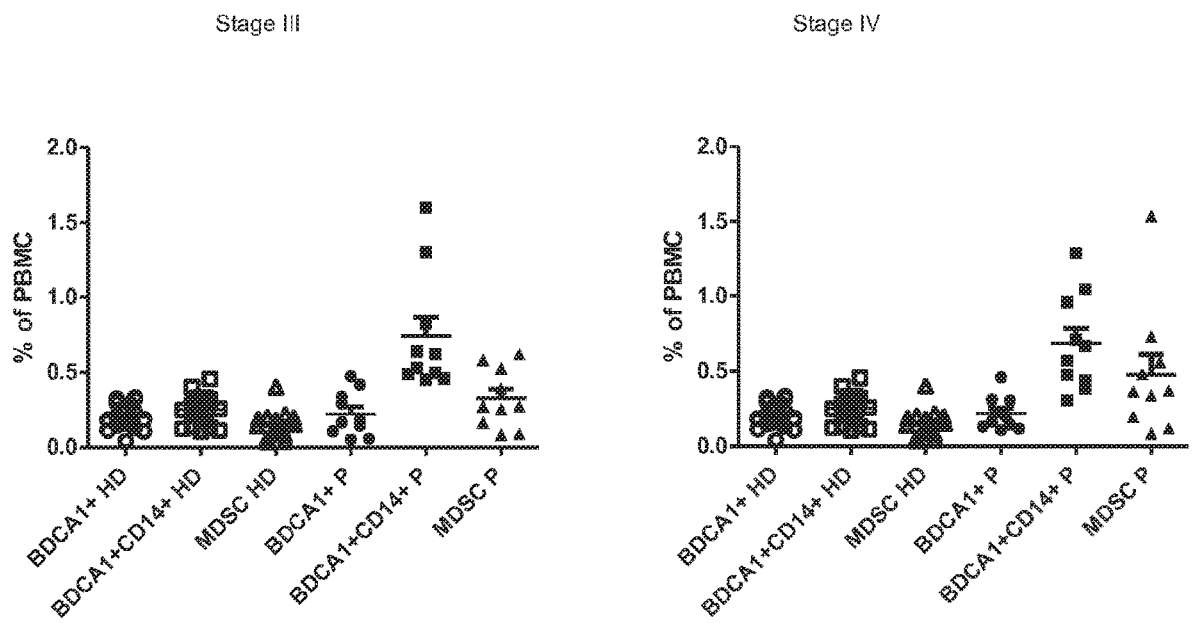

In human peripheral blood, two main populations of naturally circulating DCs can be distinguished: myeloid DCs (mDC) characterized by the expression of CD1c and the lack of expression of CD19 (CD1c+ (BDCA-1) CD19−) and plasmacytoid DCs (pDCs) characterized by the expression of CD304 (CD304+ (BDCA-4)). These subtypes differ in function, localization, and phenotype. mDCs mainly migrate to, or reside in, the marginal zone of the lymph nodes and are thought to recognize and respond to bacterial and fungal antigens. pDCs on the other hand, mainly reside in the T cell areas of lymph nodes and seem specialized for viral antigen recognition (Liu Y J. Dendritic cell subsets and lineages, and their functions in innate and adaptive immunity. Cell 2001; 106:259-262). Both mDCs and pDCs have the capacity to initiate suitable T cell responses, depending on the pathogens they encounter.

The present invention pertains to an anti-tumor DC vaccine and its manufacture as well as use. The inventors have identified a novel blood myeloid cell population, distinct for the coexpression of the DC marker CD1c (BDCA-1) and the monocytic maker CD14. This BDCA-1+ CD14+ population exerts antigen-specific immune suppression. BDCA-1+ CD14+ cells are weak inducers of T cells. Thus, targeting of this novel population in cancer patients and/or preparing BDCA1+ CD14+ cell-free DC vaccines improves the clinical efficacy of anti-tumor DC-based vaccines.

As used herein, the term "CD14+" refers to cells expressing the CD14 gene which is a component of the innate immune system. The CD14 protein, a protein with a molecular weight of 55 kD, is anchored to the cell membrane by a glycosylphosphatidylinositol tail. Generally, the term CD14+ comprises all cells which can be stained when contacted with a labeled anti-CD14 antibody or fragment thereof, namely CD14high cells and CD14low cells.

CD14high refers to cells, which stain brightly when contacted with labeled anti-CD14 antibody. This level of expression corresponds to the level as it is expressed by classical CD14high CD16− monocytes from human peripheral blood, which represent the main subset of blood monocytes and express CD14 at the highest level of all blood cells (Ziegler-Heitbrock et al., BLOOD, 21 Oct. 2010 VOLUME 116, NUMBER 16). CD14low refers to cells, which stain less brightly when contacted with labeled anti-CD14 antibody. CD14low cells display an expression level between the CD14high cells and CD14− cells, which corresponds to the level as it is expressed by non-classical CD14+ CD16high monocytes from human peripheral blood (Ziegler-Heitbrock et al., BLOOD, 21 Oct. 2010 VOLUME 116, NUMBER 16).

In one aspect, the invention refers to a cell population for use in treating cancer in a patient, wherein the cell population comprises or consists of CD1c (BDCA-1)+/CD19− cells. The term "consists" refers in this context to a cell population, in which at least 50%, at least 60%, at least 70%, at least 80%, at least 90% of all cells, preferably, 95%, 98% or 99%, or 99.9% of all CD1c+ cells of the population, are CD19−. According to the invention, the CD1c(BDCA-1)$^+$/CD19$^-$ dendritic cells (mDC) are depleted for CD1c (BDCA-1)$^+$/CD19$^-$/CD14$^+$ cells. Preferably, at least 75% of the CD14$^+$ cells are depleted.

In other words, the invention pertains in one aspect to a cell population consisting of or comprising CD1c+/CD19− dendritic cells, wherein less than or equal to 25% 25%) of these CD1c+/CD19− dendritic cells are CD1c+/CD19−/CD14+ cells; the CD1c+/CD19− dendritic cells are depleted for CD1c+/CD19−/CD14+ cells such that the cell population of CD1c+/CD19− cells comprises less than or equal to 25% (≤25%) of CD1c+/CD19−/CD14+ cells.

In preferred embodiments, the cell population of CD1c+/CD19− dendritic cells comprises less than 20%, preferably less than 15%, less than 10%, less than 5%, or most preferred, less than 1% of CD1c+/CD19−/CD14+ cells.

Since the CD1c+/CD19−/CD14− cells are also FcεR1+, this marker can also be used to distinguish these cells from CD1c+/CD19−/CD14+ cells.

In another aspect, the invention refers to a cell population for use in treating cancer in a patient, wherein the cell population comprises or consists of CD1c (BDCA-1)$^+$/CD19$^-$ dendritic cells, wherein CD1c (BDCA-1)$^+$/CD19$^-$ dendritic cells are depleted for CD1c(BDCA-1)$^+$/CD19$^-$/CD14$^+$ cells, preferably depleted for CD1c (BDCA-1)$^+$/CD19$^-$/CD14$^{high}$ cells. In another embodiment, the depletion of CD1c (BDCA-1)$^+$/CD19$^-$ dendritic cells for CD1c (BDCA-1)$^+$/CD19$^-$/CD14$^+$ cells, preferably for CD1c (BDCA-1)$^+$/CD19$^-$/CD14$^{high}$ cells, leads to a cell population in which less than or equal to 25% of the CD1c+/CD19− dendritic cells are CD1c(BDCA-1)$^+$/CD19$^-$/CD14$^+$.

In blood, CD1c (BDCA-1) is apart from mDCs also expressed on a subpopulation of CD19+ small resting B lymphocytes. For this reason, for isolation of CD1c (BDCA-1) mDCs, B cells are depleted, e.g. using the marker CD19 and/or CD20 prior to enrichment of mDCs. For isolation of the subset of CD1c (BDCA-1)+ CD14− mDCs, CD14+ cells are depleted, e.g. using the marker CD14 prior to enrichment of mDCs. After the depletion of B cells and CD14+ cells, mDCs can be labeled (e.g., using an antibody capable of binding CD1c), preferably labeled magnetically (when the CD1c antibody is coupled directly to a magnetic microbead or indirectly using biotin-conjugated CD1c antibody and anti-biotin antibody coupled to a magnetic microbead) and enriched according to the specific expression of CD1c (BDCA-1).

CD1c+/CD19− cells that are CD14+ are also CD11b- and CCR5$^{low/-}$. In contrast, CD1c (BDCA-1)+/CD19−/CD14+ cells, which exert antigen-specific immune suppression, express the molecular markers CD14, CD11b, or CCR5 and are referred to herein as "suppressive dendritic cells (DCs)".

In one embodiment of the invention, the cell population comprises or consists of CD1c+/CD19− dendritic cells, wherein less than or equal to 25%)≤25%) of these CD1c+/CD19− dendritic cells are CD1c+/CD19−/CD14+ cells together with cells that are CD304 (BDCA-4)+ (plasmacytoid DCs).

CD1c (BDCA-1)$^+$ mDCs are characterized as being: CD1c (BDCA-1)$^+$, CD11b$^-$, CCR5$^{low/-}$, CD19$^-$, CD11c-high, CD123-low, CD4$^+$, CD45RO$^+$, CD2$^+$, CD16$^-$, CD141 (BDCA-3)$^{low}$, CD303 (BDCA-2)$^-$, CD304 (BDCA-4)$^-$. They lack expression of lineage markers (CD3, CD16, CD19, CD20), and express myeloid markers, like CD13 and CD33 and Fc receptors, such as CD32, or CD64, or FcεRI.

In one embodiment of the invention, the mDCs are purified from the blood of the patient in need of a cancer treatment. This allows for the generation of a cell population of autologous mDCs, which can be administered to the patient without causing significant side effects. The blood of the patient is in one embodiment subject to apheresis, as known in the art. In one embodiment of the invention, the mDCs are activated and loaded with tumor-antigen before the administration to a patient.

pDC and mDC complement each other's functions and act synergistically for optimal immune responses. The co-administration of blood mDCs and pDCs often generates more potent and longer-lasting anti-tumor immune responses in cancer patients compared to vaccination with ex vivo-differentiated monocyte-derived DCs. Therefore, a vaccination of cancer patients by co-administration of pDCs and mDCs together with the cell population comprising or consisting of CD1c+/CD19− dendritic cells, wherein less than or equal to 25% (≤25%) of these CD1c+/CD19− dendritic cells are CD1c+/CD19−/CD14+ cells, constitutes a preferred embodiment of the invention.

Therefore, the cell composition of the invention further comprises in one embodiment also pDCs (which are CD304 (BDCA-4)$^+$) that were purified from the blood of the patient in need of a cancer treatment. Accordingly, the pDCs are autologous to the patient to whom they are to be administered.

In another embodiment, the cell composition of the invention further comprises also CD303 (BDCA-2)$^+$ cells (in particular isolated cells before culturing) that were purified from the blood of the patient in need of a cancer treatment (autologous).

CD304 (BDCA-4/Neuropilin-1)$^+$ pDCs are characterized as being CD11c$^-$, CD123high, CD4$^+$, CD45RA$^+$, CD303 (BDCA-2)$^+$, CD141 (BDCA-3)dim, CD1c (BDCA-1)$^-$, and CD2$^-$. They lack expression of lineage markers (CD3, CD14, CD16, CD19, CD20, CD56), and express neither myeloid markers, like CD13 and CD33, nor FcεRI, but they are TLR7 and TLR9 positive.

The cell population of the invention can be prepared as a pharmaceutical composition. For this purpose, the cell composition of the invention is suspended, e.g., in physiologic saline solution.

In one embodiment of the invention, the dendritic cells of the cell population are loaded with a tumor antigen or tumor peptide. In another embodiment, the dendritic cells of the cell population are loaded with an HLA binding tumor antigen or peptide.

The invention is not limited to a particular type of cancer. Instead, the cell population of the invention can be used to treat any kind of cancer. In one embodiment, the cell population is used for the treatment of melanoma, ovarian cancer or prostate cancer in a patient.

The cancer to be treated can be, for example, a melanoma, in particular a melanoma of all stages, in particular of stage III and IV, according to the Staging System of The American Joint Committee on Cancer.

The cancer to be treated can also be, for example, prostate cancer, in particular a prostate cancer of all stages, in particular of stage III and IV, according to the Staging System of The American Joint Committee on Cancer.

In another aspect, the invention refers to a cell population of dendritic cells, consisting of CD1c (BDCA-1)+/CD19– cells, wherein the cell population of CD1c+/CD19– cells contains not more than 25% of CD1c+/CD19–/CD14+ cells. In preferred embodiments, the cell population comprises less than 20%, preferably less than 15%, less than 10%, less than 5%, or most preferred, less than 1% CD1c+/CD19–/CD14+ cells of all CD1c+/CD19– dendritic cells of the population.

A method is described for producing a cell population for treating cancer in a patient, comprising the steps of purifying dendritic cells and incubating them with a tumor antigen or peptide.

The method may comprise the following steps:
Purifying dendritic cells (CD1c (BDCA-1)+/CD19–/CD14– cells) from the blood of a patient (autologous) who is in need of cancer treatment or therapy. Thereby, a cell population of autologous mDCs is obtained. This purification is performed using antibodies, namely
- at least a first antibody capable of binding to CD1c (BDCA-1) for enriching CD1c+ cells,
- at least a second antibody capable of binding to B-lymphocytes, and
- at least a third antibody capable of binding to a suppressive DC.

When performing magnetic cell sorting (MACS), first the B cells and CD14+ cells are depleted; subsequently the mDC are enriched with a CD1c antibody. For flow sorting, the sequence of steps is irrelevant.

The at least second antibody capable of binding to B-lymphocytes is in one embodiment selected from the group consisting of antibodies capable of binding to CD19 or CD20.

The at least third antibody capable of binding to a suppressive DC is in one embodiment selected from the group consisting of antibodies capable of binding to CD14, CD11b, or CCR5. The markers CD14, CD11b, and CCR5 are coexpressed on suppressive DCs. Therefore, the depletion of suppressive DCs can be performed using either one of the three markers. In one embodiment, the depletion is performed using two or all three markers from the group consisting of CD14, CD11b, and CCR5.

In the method, the CD1c (BDCA-1)$^+$/CD19$^-$ dendritic cells are depleted for CD1c (BDCA-1)$^+$/CD19$^-$/CD14$^+$ cells, preferably such that at least 75% of the CD14$^+$ cells are depleted. In certain embodiments, at least 80%, at least 85%, at least 90%, at least 95%, at least 98% or at least 99% of the CD14$^+$ cells are depleted. Alternatively, in the method the CD1c (BDCA-1)$^+$/CD19$^-$ dendritic cells are depleted for CD1c (BDCA-1)$^+$/CD19$^-$/CD14$^+$ cells such that less than or equal to 25% 25%) of these CD1c+/CD19– dendritic cells are CD1c+/CD19–/CD14+ cells.

For example, mDCs can be directly isolated from aphaeresis products. For this, a primary antibody that is capable of binding CD1c (BDCA-1)$^+$ can be used; this antibody can be conjugated with biotin or other molecule, which can be bound by a secondary antibody. A solid support, such as a bead, in particular a magnetic bead (MicroBead), is conjugated to a secondary anti-biotin-antibody capable of binding biotin or to a secondary antibody capable of binding to the molecule, which is coupled to the primary CD1c antibody. The use of a magnetic bead conjugated with the secondary anti-biotin-antibody allows for the magnetic separation of the mDCs bound to the biotinylated anti-CD1c (BDCA-1)-antibody. In one embodiment, the CD1c (BDCA-1)-antibody can be directly conjugated to a solid support such as a bead, in particular a magnetic bead (MicroBead). In another embodiment, the fully closed immunomagnetic CliniMACS isolation system (Miltenyi Biotec GmbH) is used to isolate mDCs.

Antibodies, as used herein, means intact immunoglobulin molecules as well as portions, fragments, peptides and derivatives thereof such as, for example, Fab, Fab', F(ab')$_2$, Fv, CDR regions, paratopes, or any portion or peptide sequence of an antibody that is capable of binding an antigen or epitope, and includes polyclonal antibodies, monoclonal antibodies, chimeric antibodies, fully humanized antibodies, recombinant antibodies, and monoclonal antibodies produced by transgenic animals or portions fragments, peptides and derivatives thereof. An antibody is said to be "capable of binding" a molecule if it is capable of specifically reacting with the molecule to thereby bind the molecule to the antibody. Numerous antibodies have been approved for use in humans. See, e.g., Walden, 9 Nat. Med. 269 (2004) or http://www.immunologylink.com/FDA-app-Abs.html.

The method further comprises the step of incubating the dendritic cells obtained after performing the purification steps described above with a tumor antigen or peptide.

For example, B cells are first depleted using an antibody that is capable of binding CD19, e.g. magnetic bead-coupled anti-CD19 antibodies. CD14+ cells are depleted using CD14 microbeads (i.e. with an antibody capable of binding to CD14, wherein the antibody is bound to a microbead, in particular a magnetically sortable microbead). Subsequently, CD1c (BDCA-1)+ mDCs are positively selected. For this purpose, an antibody that is capable of binding CD1c/BDCA-1 is used (anti-CD1c/BDCA-1 antibody). This can, for example, be performed with biotin-coated anti-CD1c primary antibodies and an magnetic bead-coupled secondary anti-biotin antibody.

After isolation of mDCs, mDCs may be cultured, e.g. overnight, preferably at a concentration of about 0.1×10$^6$ cells/ml to $2\times10^6$ cells/ml, under conditions that allow for the maturation of mDCs. Such mDCs may be characterized by the following criteria: increased expression of MHC class I, MHC class II, CD83 and CD86 as compared to mDC before maturation culture step.

In one embodiment of the invention, the method further comprises in addition to the isolation of CD1c+/CD19− mDC the additional step of purifying plasmacytoid dendritic cells from the blood of the patient in need of cancer treatment using, for example, CD304 (BDCA-4) antibodies.

The method further comprises, in at least one embodiment, the step of inducing the purified dendritic cells for maturation. This induction may be performed through any stimulation known in the art, e.g. by using a toll like receptor (TLR) agonist or any other stimulus allowing for maturation of DC. In one embodiment RNA-protamine complex is used as a stimulus.

According to one Example, the method is performed using the following steps:

Firstly, apheresis cells from a patient in need of cancer therapy are magnetically labeled in order to isolate the cells of interest. In particular, labeling is performed using anti-CD1c-biotin (i.e. with an antibody capable of binding to CD1c, wherein the antibody is labeled with biotin), CD14 microbeads (i.e. with an antibody capable of binding to CD14, wherein the antibody is bound to a microbead, in particular a magnetically sortable microbead) and CD19 microbeads (i.e. with an antibody capable of binding to CD19, wherein the antibody is bound to a microbead, in particular a magnetically sortable microbead). The marker CD19 is used to deplete B cells, as explained above.

Secondly, CD14+ and CD19+ cells are depleted from the starting cell composition. For this purpose, the CD14 microbeads and the CD19 microbeads are incubated with the cells from the patient and the magnetically labeled B-cells and CD14+ cells (to which CD14-microbeads and CD19-microbeads are bound, respectively) are removed. If the microbeads are magnetic, the removal of the cells bound thereto is performed using magnetic sorting system (such as provided by Miltenyi Biotech GmbH).

Thirdly, anti-biotin microbeads (i.e. with an antibody capable of binding to biotin, wherein the antibody is bound to a microbead, in particular a magnetically sortable microbead) are added to the remaining, magnetically negative cells. Optionally, for simultaneous isolation of CD1c+/CD19− mDC and CD304+ pDC, anti-biotin microbeads and CD304 (BDCA-4) microbeads (i.e. with an antibody capable of binding to CD304 (BDCA-4), wherein the antibody is bound to a microbead, in particular a magnetically sortable microbead), are added to the remaining cells.

In the fourth step, CD1c (BDCA-1)+ cells and optionally CD1c (BDCA-1)+ and CD304 (BDCA-4)+ are enriched, i.e. isolated from the population of blood cells.

In one embodiment of the invention, the CD1c (BDCA-1)$^+$/CD19$^-$ dendritic cells are depleted for CD1c (BDCA-1)$^+$/CD19$^-$/CD14$^+$ cells, such that the cell population of CD1c+/CD19− cells contains not more than 25% of CD1c+/CD19−/CD14+ cells. In alternative embodiments, at least 80%, at least 85%, at least 90%, at least 95%, at least 98% or at least 99% of the CD14$^+$ cells are depleted, such that the cell population of CD1c+/CD19− cells contains not more than 25% of CD1c+/CD19−/CD14+ cells.

In one embodiment of the invention, pDCs and mDCs are loaded with different antigens or peptides or fragments thereof.

In another aspect, the invention refers to the use of a kit for producing a cell population for treating cancer in a patient, in particular in a method as described above and herein. Such a kit comprises or consists of the following components:

An antibody capable of binding to CD1c (BDCA-1),
An antibody capable of binding to a monocyte, preferably to suppressive DCs,
An antibody capable of binding to a B cell, and optionally
An antibody capable of binding to CD304 (BDCA-4).

An antibody capable of binding to a suppressive DCs may be selected from the group consisting of CD14, CD11b, and CCR5. An antibody capable of binding to a B cell may be selected from the group consisting of antibodies capable of binding to CD19 or CD20.

In one embodiment of said use, the further comprises an HLA binding tumor antigen. The tumor antigen (e.g. a tumor peptide) should be chosen according to the cancer that is to be treated.

In another aspect, the invention refers to a method for treating cancer comprising the step of administering a cell population as described herein to a human cancer patient who is in need of such treatment. According to one embodiment of the method, a blood dendritic cell population (e.g., CD1c (BDCA-1)+/CD19−/CD14− cells or CD1c+/CD19− cells with less than or equal to 25% of CD1c+/CD19−/CD14+ and preferably CD1c (BDCA-1)+/CD19−/CD14− cells, or CD1c+/CD19− cells with less than or equal to 25% of CD1c+/CD19−/CD14+ in addition to CD304 (BDCA-4)+ cells) is administered to a patient suffering from cancer.

The dose rate of DCs to be administered usually lies between $10^3$ and $10^9$, preferably between $10^5$ and $10^7$ per injection, but needs to be adapted to the patient to be treated. The tumor antigen or tumor peptide-loaded DCs can be administered intranodally into a lymph node region, preferably under ultrasound guidance.

Usually, two to four intranodal injections may be given once every one to four weeks, optionally followed by a DTH challenge (DTH=delayed-type hypersensitivity). A DTH response is a measure of the ability to immunize a patient to a tumor cell or specific tumor antigen and serves here as a control. In the absence of disease progression, patients may be eligible for maintenance cycles consisting of further vaccinations and possibly a DTH challenge, each, for example, with a 3 to 7 months interval, preferably with a 6 months interval.

Usually, between $1\times10^5$ and $1\times10^7$ cells of a population of mDCs and pDCs are administered.

The mDCs and pDCs are usually immature (showing a low expression level of CD83, CD86, MHC class I and MHC class II) when they are isolated from the blood of a patient. Therefore, in one embodiment of the invention, mDC are cultured and matured by stimulation, e.g. with RNA-protamine (upregulation of CD83, CD86, MHC class I and MHC class II expression).

In one embodiment, mDCs are directly isolated from aphaeresis products using the fully closed immunomagnetic CliniMACS isolation system including magnetic bead-coupled antibodies (Miltenyi Biotec GmbH, Germany).

EXAMPLES

Materials & Methods

Cell isolation: In order to isolate the different subsets, first PBMCs were isolated from healthy donors or stage III or stage IV melanoma patients using ficoll-paque gradient (Lucron Bioproducts). When indicated the total BDCA1-expressing population (that includes BDCA1+ DCs and BDCA1+ CD14+ population) was isolated from PBMCs using the BDCA1+ DC isolation kit (Miltenyi Biotec GmbH, Bergisch Gladbach, Germany), followed by monocyte isolation by applying anti-CD14 microbeads (Miltenyi Biotec). The two BDCA1-expressing subsets were late discriminated based on CD14 expression, by using anti-CD14-PerCP (BD Biosciences, San Jose, Calif.).

In order to separately isolate BDCA1+ DCs, BDCA1+ CD14+ cells, monocytes and myeloid-derived suppressor cells (MDSCs) we resorted to FACS, which was preceded by a depletion of T, B and NK cells from PBMCs. First PBMCs were treated by FcR blocker (Miltenyi Biotec) to avoid any aspecific binding of antibodies, then PBMCs were treated with anti-CD3-FITC, anti-CD20-FITC, anti-CD56-FITC (all from BD Biosciences) and anti-CD19– FITC (Dako Cytomation, Glostrup, Denmark) followed by treatment with anti-FITC microbeads (Miltenyi Biotec) and magnetic-activated cell sorting. The depleted PBMCs were then prepared for flow-activated cell sorting (FACS) by labeling them with the following antibodies: Lineage cocktail-FITC, anti-CD14-PerCP, anti-HLA-DR-PE-Cy7 (all from BD Biosciences) and anti-BDCA1-PE (Miltenyi Biotec). The four subsets were isolated using FACS Aria (BD Biosciences). The FACS gating strategy is displayed in FIG. 8.

Naïve CD4+ T cell population was isolated from PBMC by first isolating the total CD4+ T cell population using MACS CD4+ T cell isolation kit (Miltenyi Biotech). Subsequently, nave CD45RA+CD45RO– CD4+ T cells were separated from memory T cells by applying anti-CD45RO-PE (Dako Cytomation) and anti-PE beads (Miltenyi Biotech). Purity levels higher than 98% were achieved, determined by flow cytometry. Phenotype: The phenotype of BDCA1+ DCs, BDCA1+ CD14+ cells and MDSCs was compared by flow cytometry. The total BDCA1+ population and the monocyte population were isolated by MACS as described above. BDCA1+ CD14+ cells were distinguished from BDCA1+ DCs by labeling with anti-CD14-PerCP (BD Biosciences). The following antibodies were used to determine the phenotype: anti-CD1a-FITC, anti-CD33-APC, anti-CD206-PE (all from BD Biosciences), anti-CD16-APC (Miltenyi Biotec), and anti-CD209-PE (Beckman Coulter).

Uptake assay: The antigen-uptake capacity of BDCA1+ DCs, BDCA1+ CD14+ cells and monocytes was determined by measuring to what extent they can take up Alexa-488-labeled bovine serum albumin (BSA). $100 \times 10^3$ of BDCA1+ cells (isolated by MACS as described above) or monocytes were cultured in X-VIVO 15 medium (Lonza) in the presence or absence of 1 mg/ml of BSA-Alexa-488 at 37° C. for 5, 15, 30 or 60 minutes. Similar cultures were performed at 4° C. to measure any background readings resulting from spontaneous binding of BSA. After the culture period, BDCA1+ cells were stained with anti-CD14-PerCP, to discriminate BDCA1+ CD14+ cells from BDCA1+ DCs. Uptake of BSA-Alexa 488 by different cell subsets was measured by flow cytometry (FACS Calibur, BD Biosciences).

Cellular subset activation: After isolation, the cellular subsets were cultured in a round bottom 96 well-plate ($50 \times 10^3$ cells for cytokine detection and $10 \times 10^3$ for co-culture with T cells) using X-VIVO 15 medium supplemented with 5% human serum (HS, bloodbank, Rivierenland). These cells were either left unstimulated or they were stimulated with GM-CSF, LPS or poly IC (both from Sigma-Aldrich, St. Louis, Mo. USA) and incubated over night at 37° C. The expression of co-stimulatory molecules after activation was determined using anti-CD80-APC and anti-CD86-APC (both from BD Biosciences). Cytokine production by these subsets was determined by measuring IL-6, IL-12, TNF-α and IL-10 using a standard sandwich EILSA.

Mixed lymphocyte reaction (MLR): The ability of the subsets to induce T cell proliferation and cytokine production was tested in an MLR. $10 \times 10^3$ of unstimulated or stimulated cells (as above) were added to $100 \times 10^3$ freshly isolated allogeneic nonadherent peripheral blood lymphocytes (PBLs) from a healthy donor. IFN-γ and IL-10 production by those T cells was determined in 48 hours supernatants by a standard sandwich ELISA. Proliferation was determined by [$^3$H]-thymidine incorporation. The incorporated [$^3$H]-thymidine was measured after 16 h by liquid scintillation spectroscopy.

The capacity of the subsets to induce nave CD4+ T cell proliferation was determined by co-culturing 10)($10^3$ of unstimulated or stimulated cells (as above) with $50 \times 10^3$ allogeneic nave CD4+ T cells. When mentioned, anti-PD-L1 (R&D systems) or isotype control antibodies were added. Proliferation of T cells was determined by [$^3$H]-thymidine incorporation after 3 to 4 days of co-culture.

KLH-specific suppressor assay: BDCA1+ DCs, BDCA1+ CD14+ cells, monocytes and MDSCs were isolated by FACS from melanoma patients as mentioned above. $20 \times 10^3$ cells of each subset, in triplicates, were cultured overnight at 37° C. in X-VIVO 5% HS. Meanwhile, the extra monocytes were pulsed by KLH over night at 37° C. Autologous CD4+ population was also isolated by MACS CD4+ T cell isolation kit (Miltenyi Biotech) and kept in X-VIVO 5% HS at 4° C. The following day, the isolated CD4+ T cells, which include KLH-specific T cells, were stimulated by KLH-pulsed monocytes in the presence or absence of one of the four subsets. T cell proliferation was determined by [$^3$H]-thymidine incorporation after 24 to 48 hours of co-culture.

Results

Figure 1B:
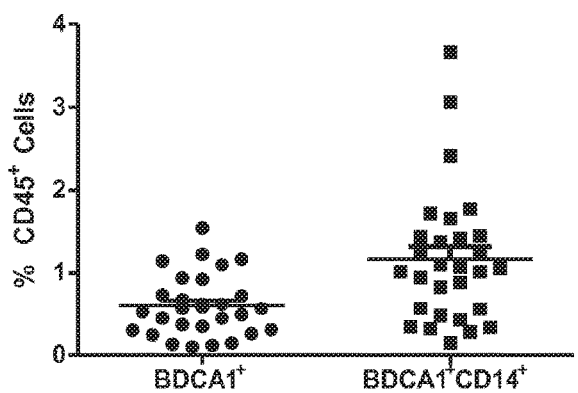

A Unique Myeloid Subset Characterized by the Coexpression of CD1c (BDCA1) and CD14 is Associated with Tumors In order to determine whether progressive tumors may influence BDCA1$^+$ DC counts in circulation, the percentages of this population was assessed in peripheral blood of stage III/IV melanoma patients and healthy donors. A trend of lower BDCA1$^+$ DC percentages in melanoma patients was observed, though it was not significant (FIG. 1A). Interestingly, a subset of BDCA1$^+$ CD11c$^+$ HLA-DR$^{hi}$ population coexpressing the monocytic marker CD14 (for the gating strategy, see also FIG. 8) was significantly elevated in melanoma patients in comparison to healthy donors (FIG. 1A). The observed increase of this BDCA1$^+$ CD14$^+$ population was concurrent with a significant increase in the percentages of circulating myeloid-derived suppressor cells (MDSCs), characterized as CD14$^+$ HLA-DR$^{Low}$ (for the gating strategy, see also FIG. 8). The presence of the BDCA1$^+$ CD14$^+$ population is not restricted to circulation as this population was also detected in inflammatory tumor ascites from ovarian cancer patients. Factually, ascites material displayed significantly higher content of the BDCA1$^+$ CD14$^+$ population in comparison to BDCA1$^+$ DCs (FIG. 1B).

Figure 1C:
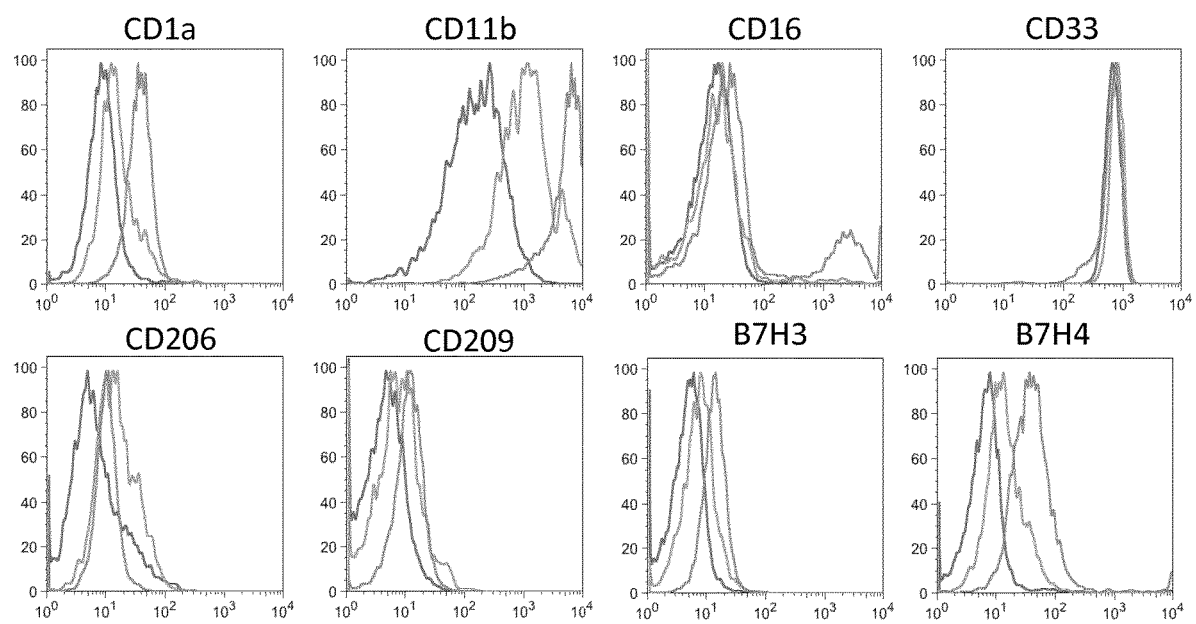

Although the existence of a CD14$^+$ DC subset has been extensively described in the skin dermal compartment, such a population has never been investigated in blood. In order to determine whether this BDCA1$^+$ CD14$^+$ population is actually another myeloid DC subset, the phenotype of this population was analyzed in comparison to BDCA1$^+$ DCs and monocytes. In addition to the high expression of CD11c and HLA-DR (not shown), typical for BDCA1$^+$ DCs (blue line, left line), the BDCA1$^+$ CD14$^+$ (green line, middle line)

population also expressed the monocytic marker CD11b at higher levels than BDCA1$^+$ DCs yet lower than monocytes (orange line, right line) (FIG. 1C). Moreover, the BDCA1$^+$ CD14$^+$ population lacked the expression of CD16 that is characteristic for a subset of monocytes and CD16$^+$ subset of myeloid DCs. The three populations shared high expression of the myeloid marker CD33 and almost absent expression of CD1a, DC-SIGN, and CD206 (mannose receptor) (FIG. 1C). Collectively, these data clearly demonstrate a novel cell population that is associated with progressive tumors and bares phenotypcial similarities to both BDCA1$^+$ DCs and monocytes.

Figure 2A:
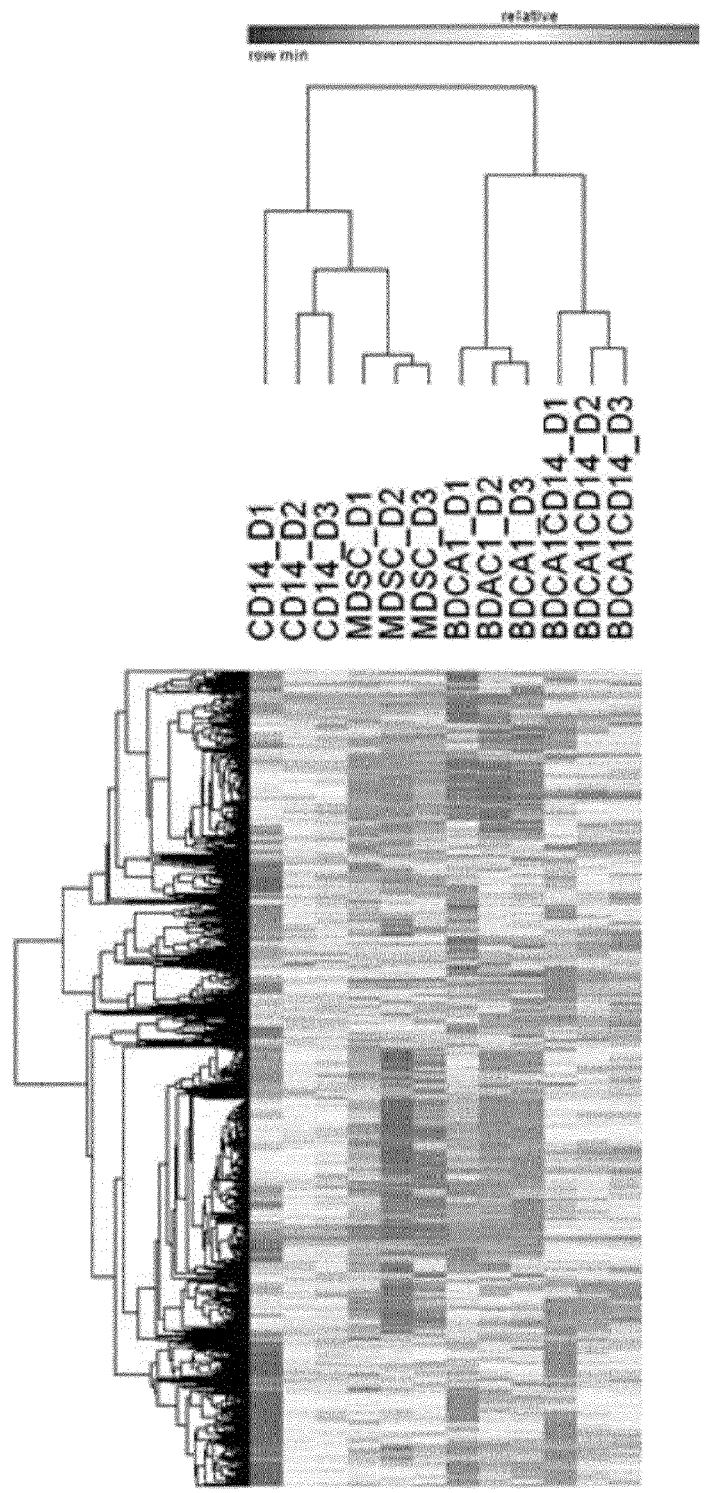
FIG. 2A: BDCA1+CD14+ population is a unique subset as shown by transcriptome analysis.
Figure 2B:
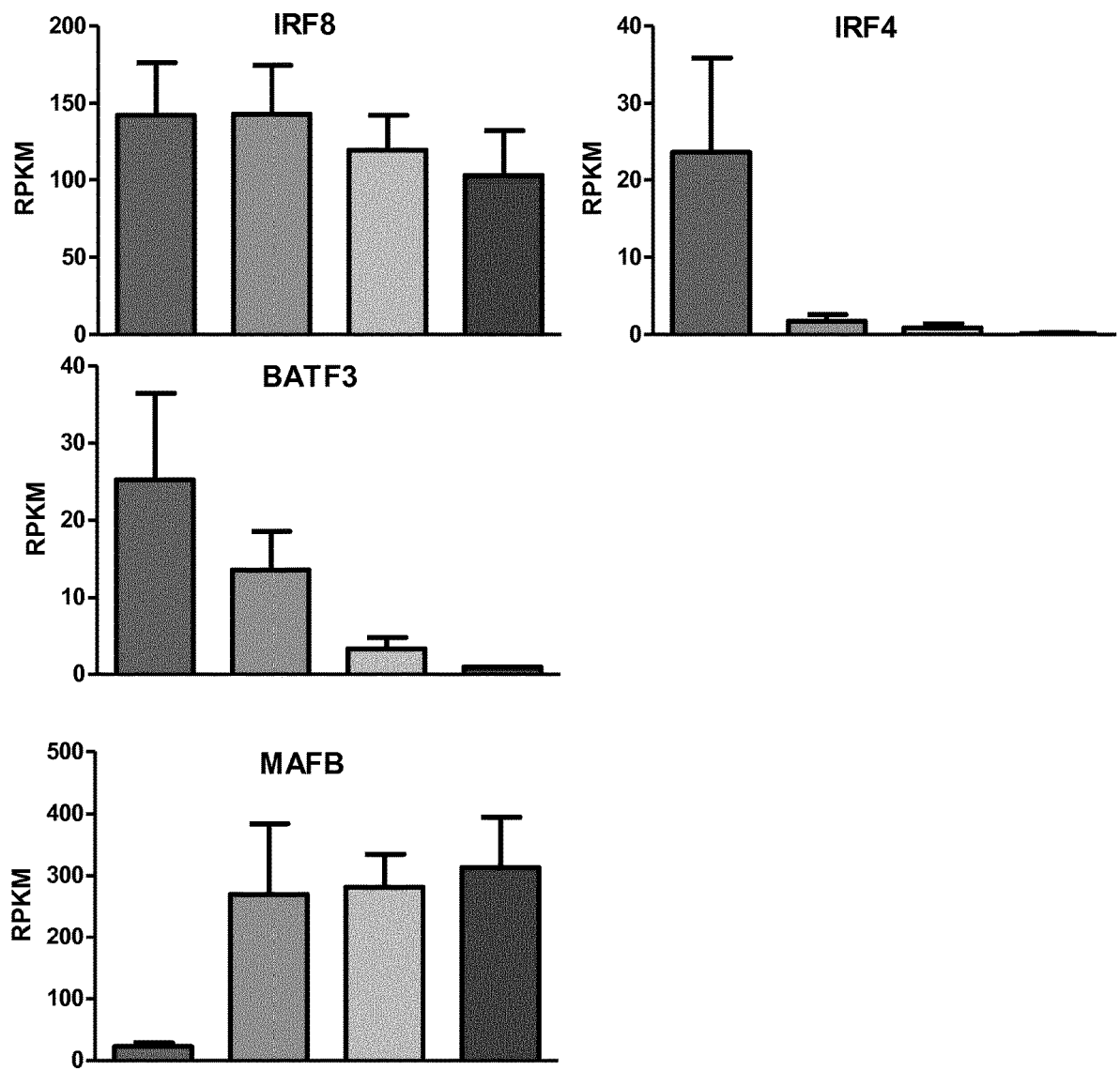
FIGS. 2B-2C: Expression of transcription factors that were described to be involved in myeloid development in mice.
Figure 2C:
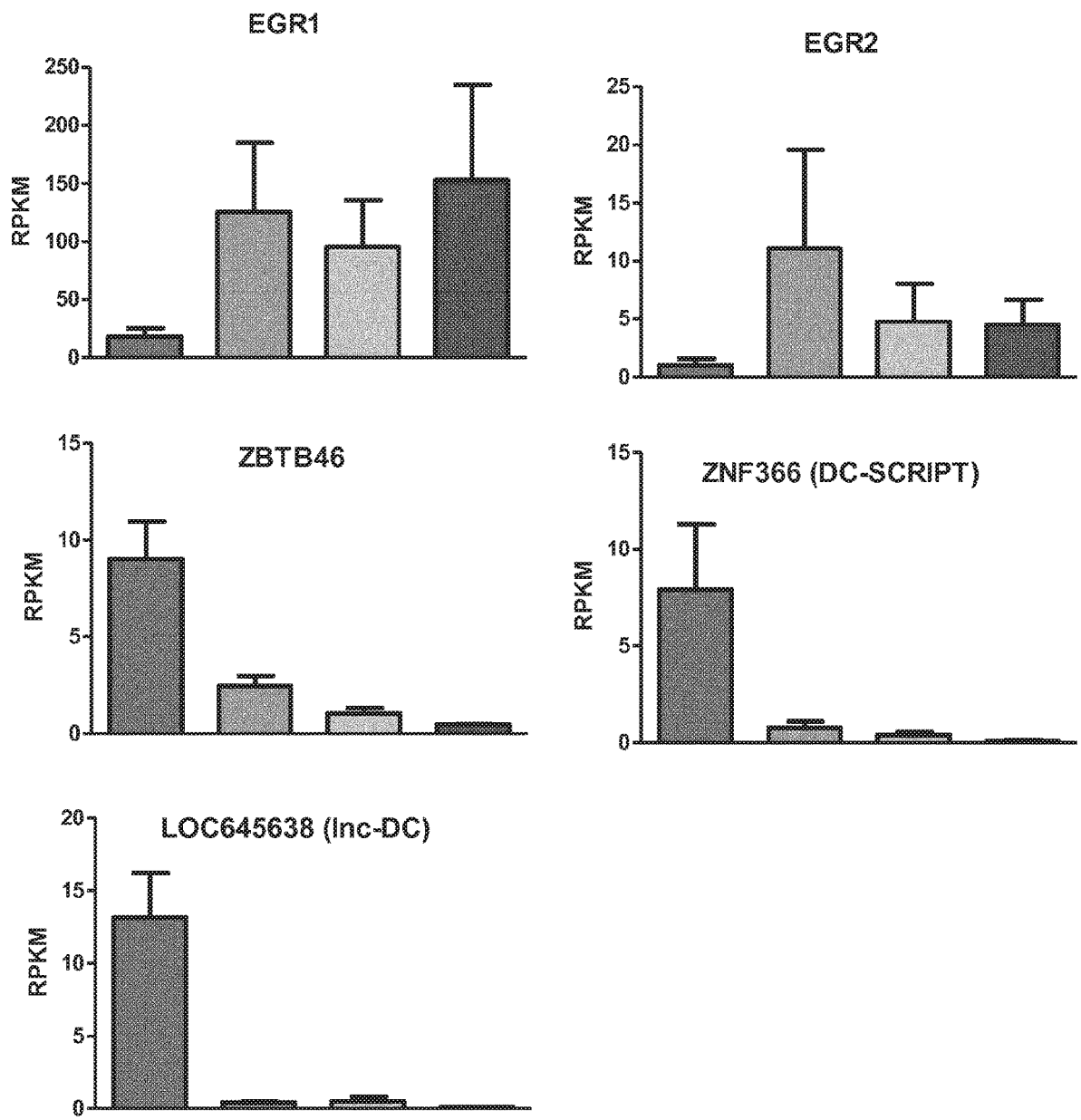
Figure 2D:
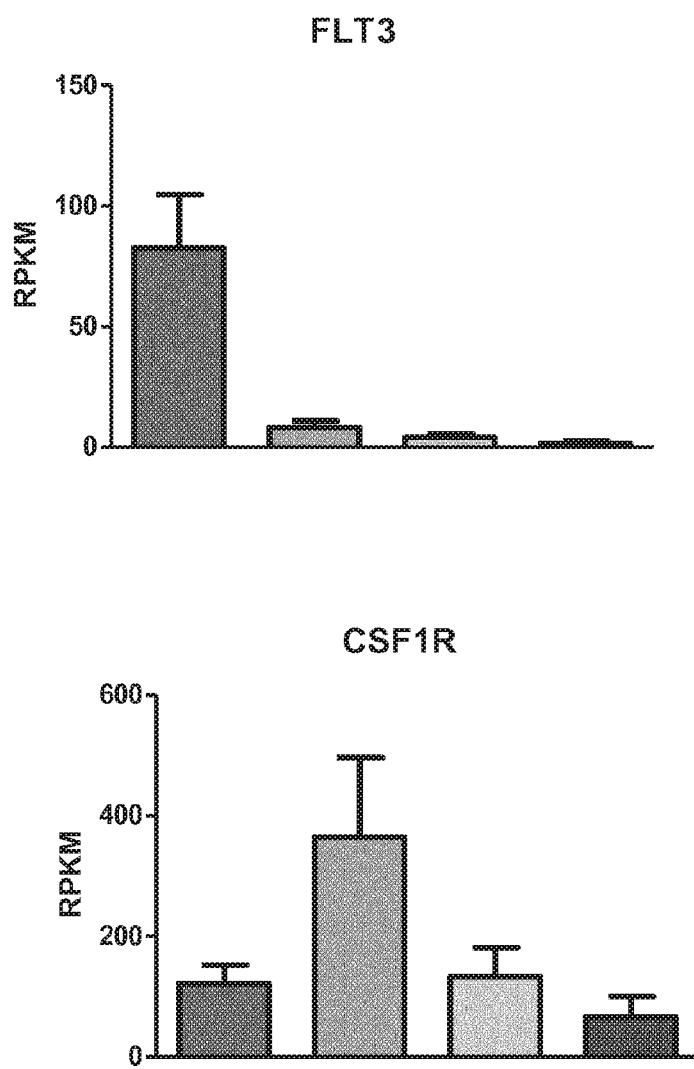
FIG. 2D: Expression of growth factor receptors that were described to be involved in myeloid development in mice.

Transcriptome and Antibody Microarray Analyses of BDCA1$^+$ CD14$^+$ Cells Reveals a Distinct Population that is Closely Related to BDCA1$^+$ DCs Since the BDCA1$^+$ CD14$^+$ population shares the expression of specific markers with both monocytes and BDCA1$^+$ DCs, further analysis was required to determine the uniqueness of this population and that it is not simply a DC or a monocyte subpopulation. To address this question, the trascriptomes of BDCA1$^+$ CD14$^+$ cells, BDCA1$^+$ DCs, monocytes and MDSCs isolated from the blood of 3 healthy donors were compared by RNA sequencing. Hierarchical clustering of the different samples using the 5000 highest expressed genes clearly portrays BDCA1$^+$ CD14$^+$ cells as a unique population. Although this population shares, to varying extents, gene expression with the three other cellular types, BDCA1$^+$ CD14$^+$ population was more closely related to BDCA1$^+$ DCs than to other populations (FIG. 2A). In order to gain more insight into the origin and development of BDCA1$^+$ CD14$^+$ cells, the inventors assessed the expression of transcription factors (FIGS. 2B-2C) and growth factor receptors (FIG. 2D) that were described to be involved in myeloid development in mice. Although the RNA expression of IRF4, BATF3 and FLT3, all crucial for DC development in mice, was highest in BDCA1$^+$ DCs (blue bars, first from left), BDCA1$^+$ CD14$^+$ (green bars, second from left) cells had higher expression when compared to monocytes (orange bars, third from left) and MDSCs (purple bars, fourth bar from left). RNA expression of IRF8, another important factor for DC development, was uniform across the four populations. Similarly, RNA expression of ZBTB46 and ZNF366 (DC-SCRIPT), both transcription factors that are specific for DC lineage in mice and humans, was highest in BDCA1+ DCs followed by BDCA1$^+$ CD14$^+$ cells. Moreover, of the long noncoding RNA LOC645638 (lnc-DC), which was revealed to be specifically expressed by DCs[24], was almost exclusively expressed by BDCA1$^+$ DCs. In contrast, BDCA1$^+$ CD14$^+$ cells, monocytes and MDSCs had equally higher RNA expression of MAFB, EGR1 and EGR2, all transcription factors involved in macrophage differentiation in mice, than BDCA1$^+$ DCs. Furthermore, RNA expression of CSF1R, also involved in macrophage differentiation in mice, was highest BDCA1$^+$ CD14$^+$ cells, whereas other population had equal expression levels. Conclusively, BDCA1$^+$ CD14$^+$ cells form a distinct population with a unique gene expression profile.

Figure 3:
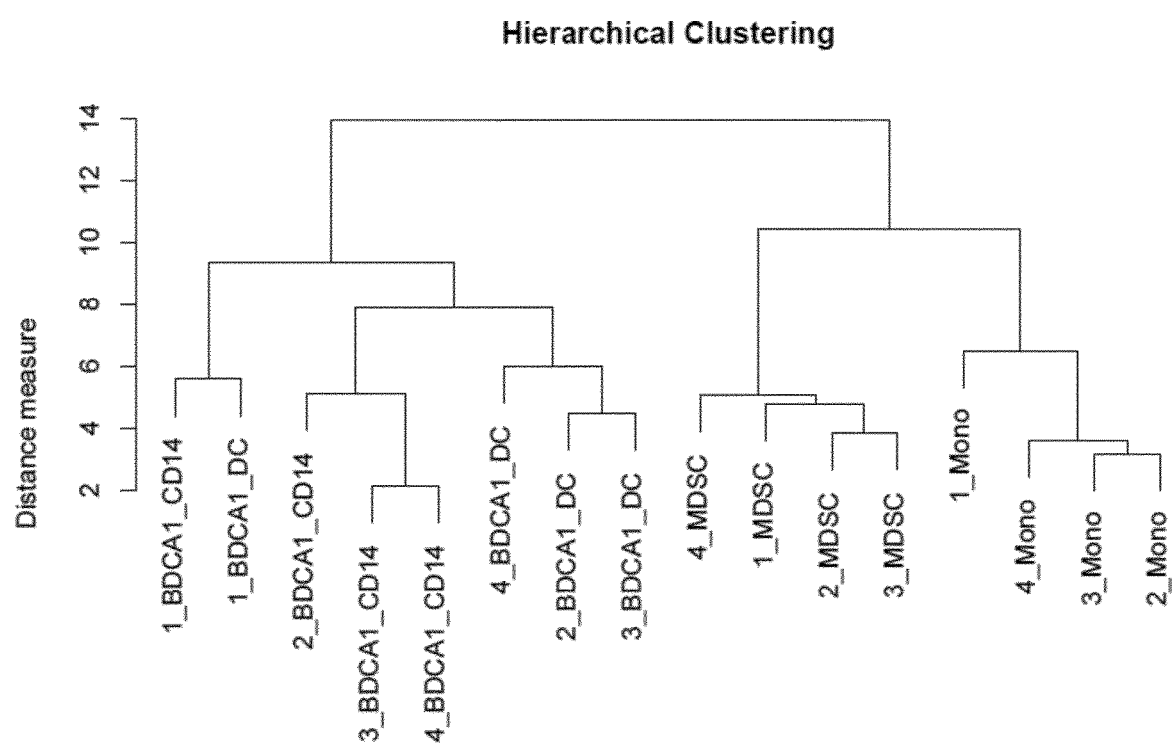
FIG. 3: BDCA1+CD14+ population is a unigue subset as shown by multiplex analysis.

In addition to the RNA expression analysis, the differential protein expression of CD molecules, HLA molecules, chemokines and cytokines (Table 1) were studied in the three cell populations using antibody microarrays (Multiplex analysis). Hierarchical clustering of differentially expressed proteins revealed a similar pattern to RNA expression data with BDCA1$^+$ CD14$^+$ cells clustering closer to BDCA1+ DCs (FIG. 3). Thus, protein analysis further supports the uniqueness of the BDCA1$^+$ population.

BDCA1$^+$ CD14$^+$ Cells Possess DC Functional Features

Figure 4A:
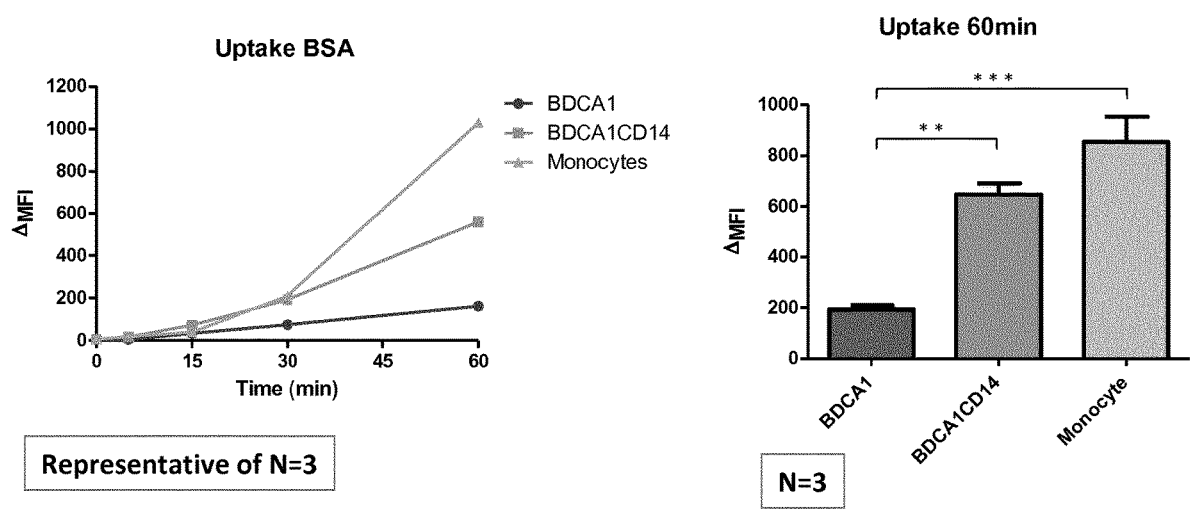

Although RNA and protein analyses insinuate close relation between BDCA1$^+$ CD14$^+$ cells and BDCA1$^+$ DCs, functional similarities between the two subsets ought to be determined as an additional proof of this close relation. DCs by definition are professional antigen presenting cells that can mount up adaptive immune responses by activating T cells. Therefore, the inventors initially assessed the capacity of BDCA1$^+$ CD14$^+$ cells to take up antigens from surrounding environment. For that purpose the uptake of fluorescently-labeled bovine serum albumin (BSA) by BDCA1$^+$ CD14$^+$ cells, BDCA1$^+$ DCs or monocytes was determined by means of flow cytometry following incubation for different periods of time at 37° C. In order to avoid any fluorescence resulting from spontaneous binding of BSA to the cells, 4° C. controls were taken along for every time point and the mean fluorescence intensity (MFI) values measured in these 4° C. samples were subtracted from those measured in the 37° C. samples (ΔMFI). As shown in FIG. 4A, BDCA1$^+$ CD14$^+$ cells display significantly higher antigen uptake capacity reflected by higher ΔMFI values already after 15 minutes of incubation with fluorescently labeled BSA. Interestingly, this uptake assay revealed monocytes to be the best in this process, though the differences between BDCA1$^+$ CD14$^+$ cells and monocytes were not significant (FIG. 4A, left panel).

Figure 4B:
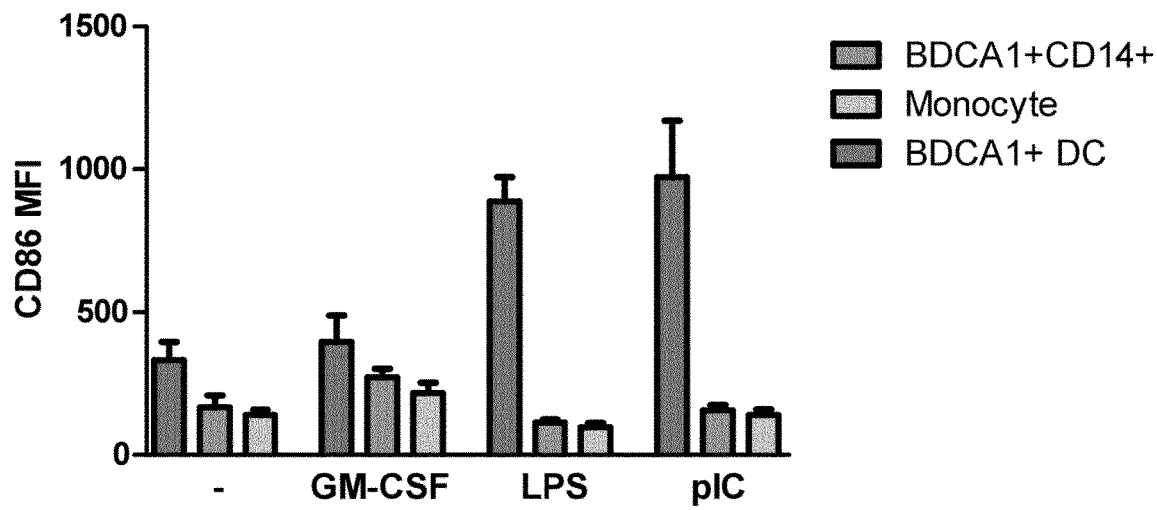
Figure 4B:
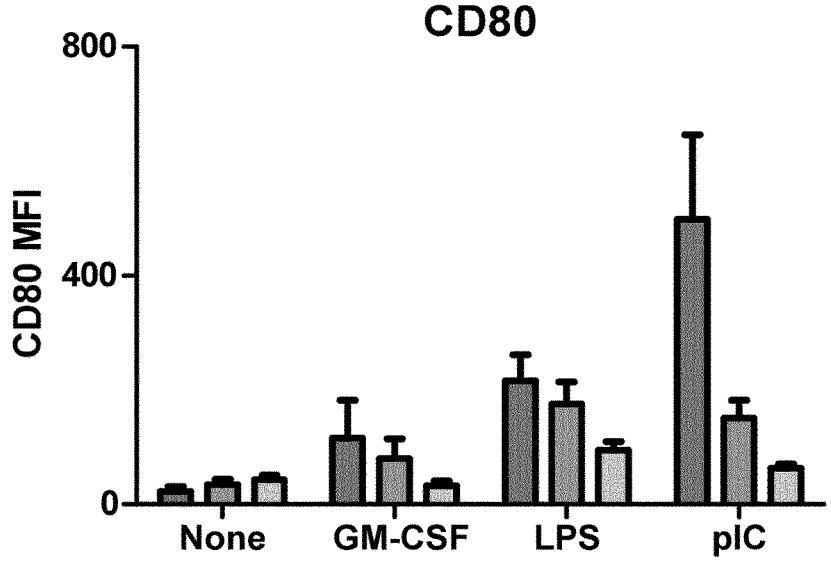
Figure 4C:
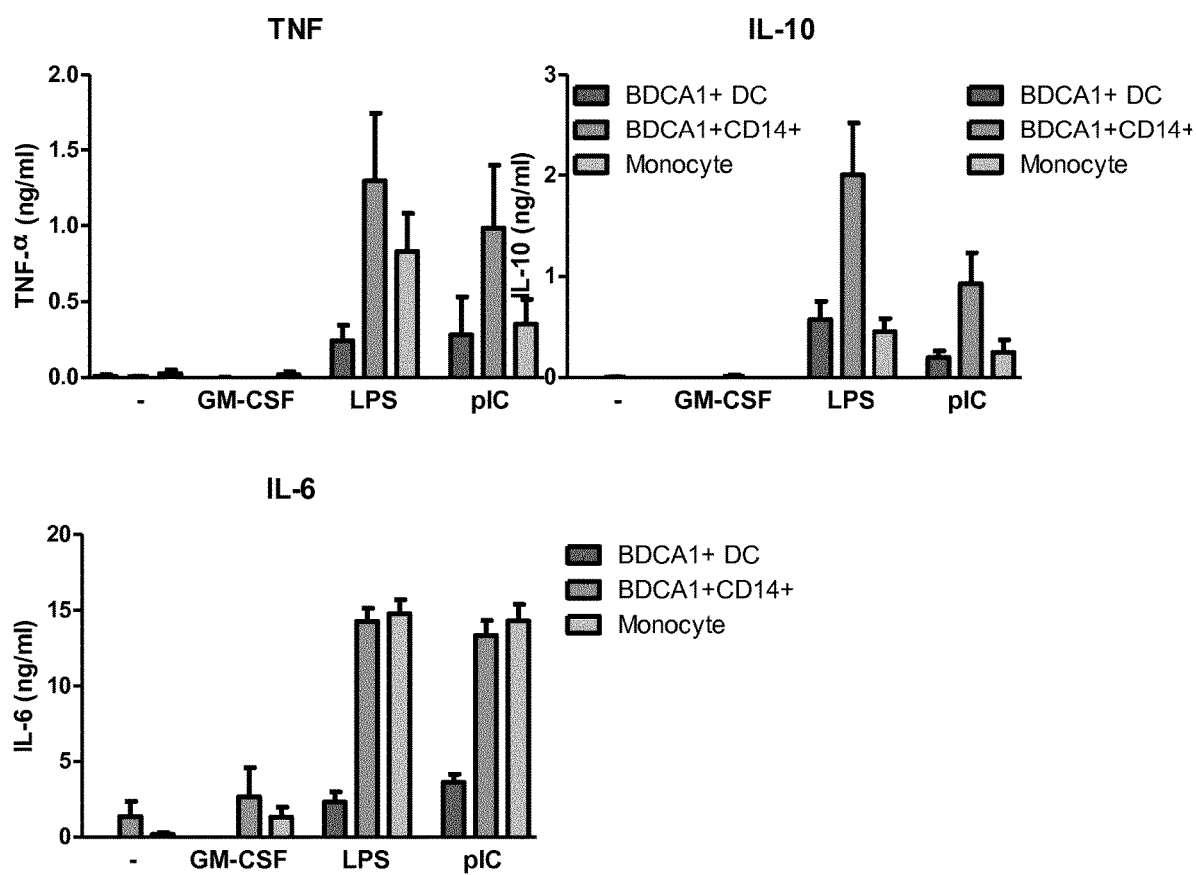
Figure 4D:
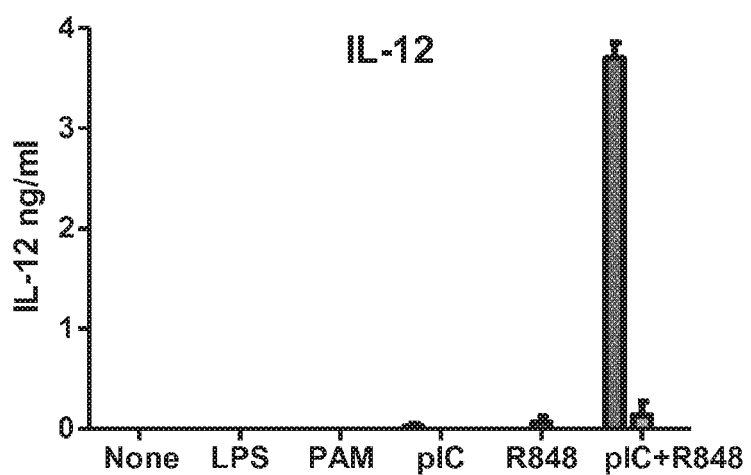

A major hallmark of DCs is their ability to sense danger signals and respond to such signals by expressing co-stimulatory molecules and secreting cytokines, a process also referred to as maturation. In order to determine to what extent BDCA1$^+$ CD14$^+$ cells own this quality, differential co-stimulatory molecules expression and cytokine production among BDCA1$^+$ CD14$^+$ cells, BDCA1$^+$ DCs and monocytes was determined following stimulation with GM-CSF, commonly used in cancer immunotherapy, LPS (TLR4 ligand) and pIC (TLR3 ligand). Whereas BDCA1$^+$ DCs responded to both LPS and pIC, by upregulating the co-stimulatory molecules CD86 and CD80, BDCA1$^+$ CD14$^+$ cells reacted to this stimulation by solely upregulating CD80 expression. Monocytes on the other hand modestly upregulated CD80 expression only in response to LPS and less efficiently than BDCA1$^+$ CD14$^+$ cells and BDCA1$^+$ DCs (FIG. 4B). Furthermore, all three populations responded by secreting profile of cytokines. Whereas BDCA1+ DCs were characterized by secreting IL-12, which was lacking in the two other subsets, BDCA1$^+$ CD14$^+$ cells significantly produced higher amounts of TNF-α in comparison to BDCA1$^+$ DCs and monocytes (FIGS. 4C-4D). Both BDCA1$^+$ CD14$^+$ cells and monocytes produced higher amounts of IL-6 than BDCA1$^+$ DCs. BDCA1$^+$ CD14$^+$ cells produced higher amounts of the inhibitory cytokine IL-10 (FIGS. 4C-4D).

Figure 5A:
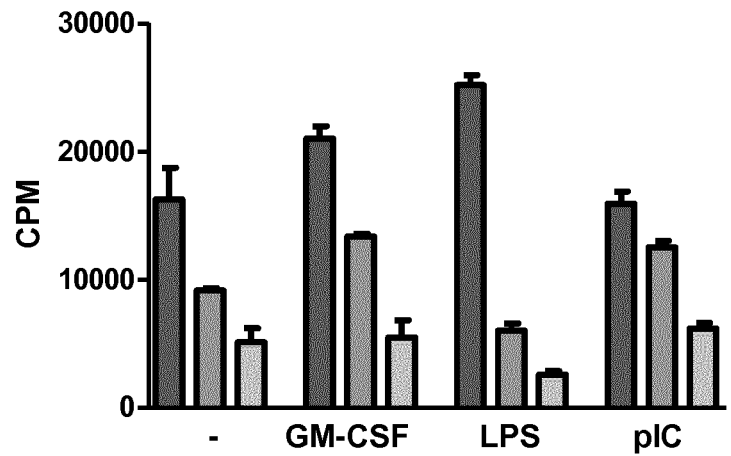
FIG. 5A: MLR
Figure 5A:
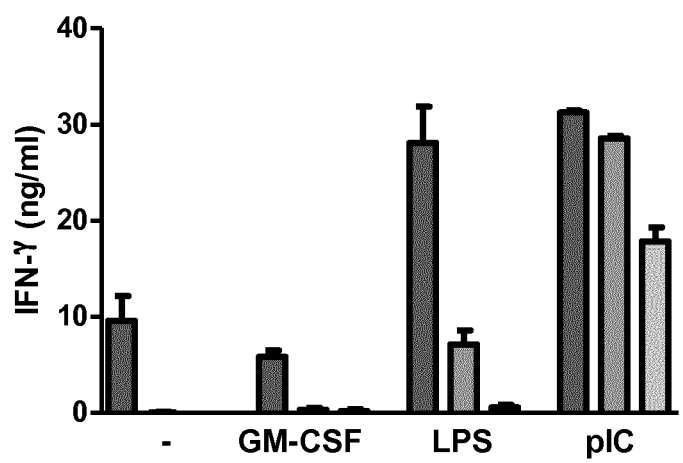
Figure 5A:
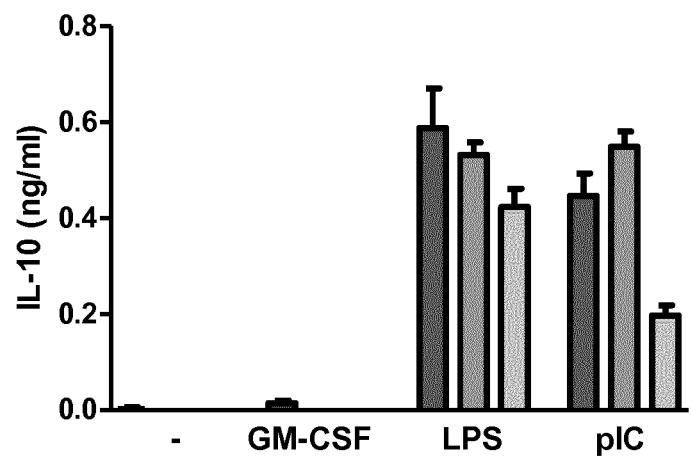
Figure 5B:
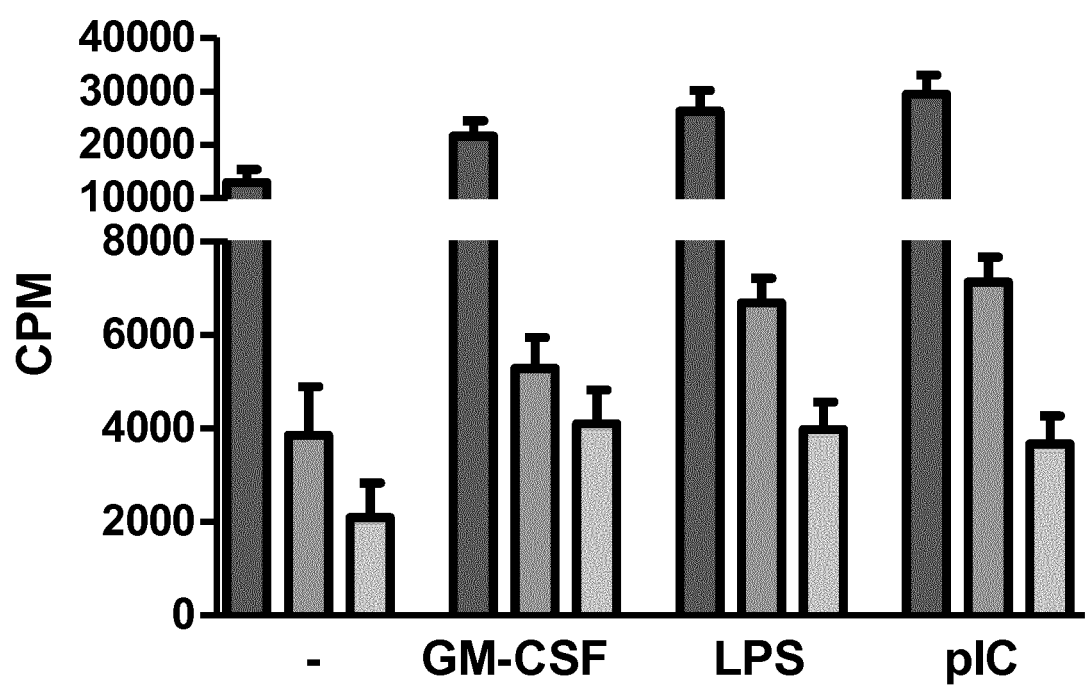
FIG. 5B: Naïve T cell stimulatom capacity.

The observed differences in maturation speculate for functional variations in activating T cells. Therefore, the T cell stimulatory capacity of BDCA1$^+$ CD14$^+$ cells, BDCA1$^+$ DCs and monocytes was assessed in two settings. The first setting is a mixed leukocyte reaction (MLR), where either of these populations was used to trigger the proliferation of allogeneic peripheral blood lymphocytes (PBLs), which was determined by $^3$[H]-labeled thymidine incorporation. As anticipated from maturation data mentioned above, the ability of BDCA1$^+$ CD14$^+$ (green bars, in the middle of the three bars) cells to induce PBL proliferation was higher than monocytes (orange bars, right) and lower than BDCA1$^+$ DCs (blue bars, left; FIG. 5A). This observation persists whether BDCA1$^+$ CD14$^+$ cells were stimulated by a TLR ligand or not. Assessing cytokines' levels in the supernatants of stimulated PBLs revealed that BDCA1$^+$ CD14$^+$ cells-induced PBLs produced more IFN-y than monocyte-induced PBLs and lower than BDCA1+ DCs-induced PBLs, whereas IL-10 was produced at equal levels by PBLs induced by any of the cellular subsets (FIG. 5A). A more refined alternative for assessing T cell stimulatory capacity of the different subsets is by determining to what extent they are capable of inducing the proliferation of allogeneic nave CD4+ T cells. Similar to the MLR setting, BDCA1+ CD14+ cells induced higher CD4+ T cell proliferation than monocytes and lower than BDCA1+ DCs (FIG. 5B).

Collectively, BDCA1+ CD14+ cells are endowed with DC features as demonstrated by a high antigen uptake capacity, the ability to mature in response to TLR stimulation and inducing T cell proliferation, albeit to a lesser extent in comparison to conventional BDCA1+ DCs.

Figure 6A:
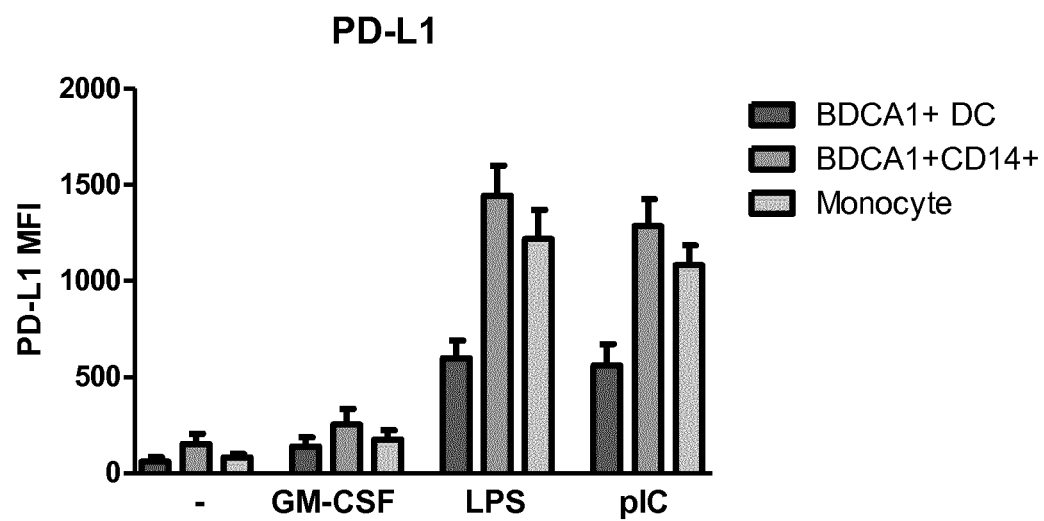
Figure 6B:
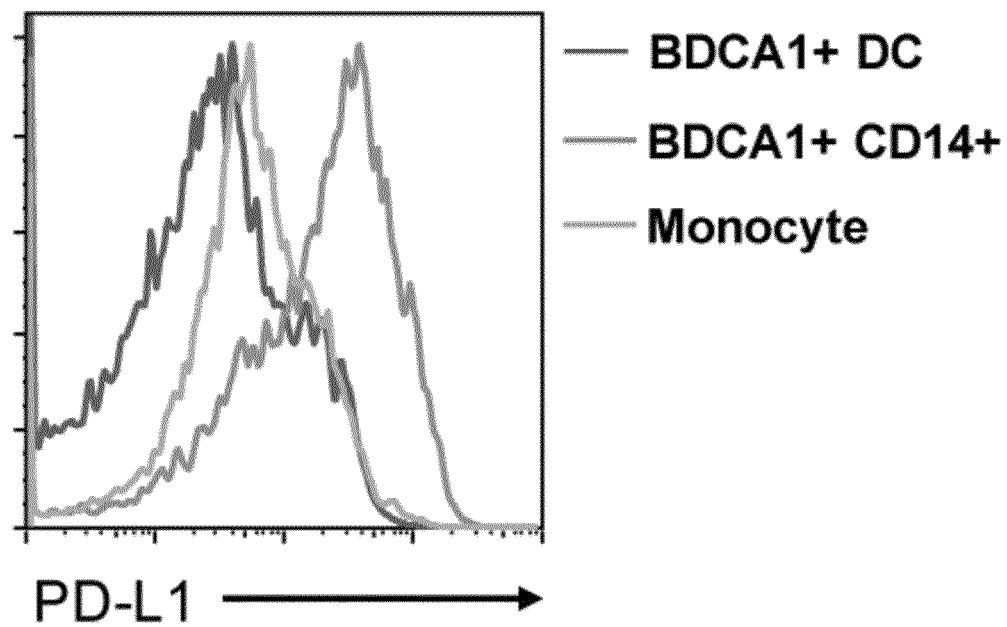
Figure 6B:
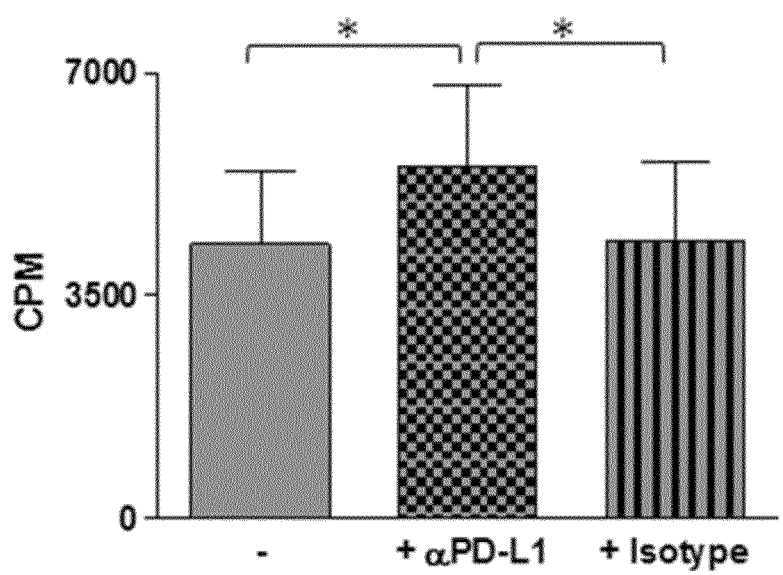

BDCA1+ CD14+ Population is Characterized by Elevated PD-L1 Expression that Dampens its T Cell Stimulatory Capacity The DC-derived co-stimulatory Signal II is vital for T cell activation. In addition to co-stimulatory molecules, Signal II may also be mediated through co-inhibitory molecules expressed by DCs and leading to attenuated T cell responses. Among these co-inhibitory molecules is PD-L1 and PD-L2. Whereas PD-L2 is not expressed by any of the subsets, either with or without stimulation (data not shown), PD-L1 is expressed following TLR ligation by all of subsets. However, BDCA1+ CD14+ cells demonstrate significantly higher levels of PD-L1 in comparison to BDCA1+ DCs (FIG. 6A). In order to assess the effect of PD-L1 expression on the T cell stimulatory capacity of BDCA1+ CD14+ cells, PD-L1 molecules were blocked by antibodies during activation of nave CD4+ T cells. Indeed neutralizing PD-L1 molecules significantly enhanced BDCA1+ CD14+ cells-induced T cell proliferation (FIG. 6B). Thus, high PD-L1 expression by BDCA1+ CD14+ cells is involved in hampering the functionality of this cell population.

Figure 7A:
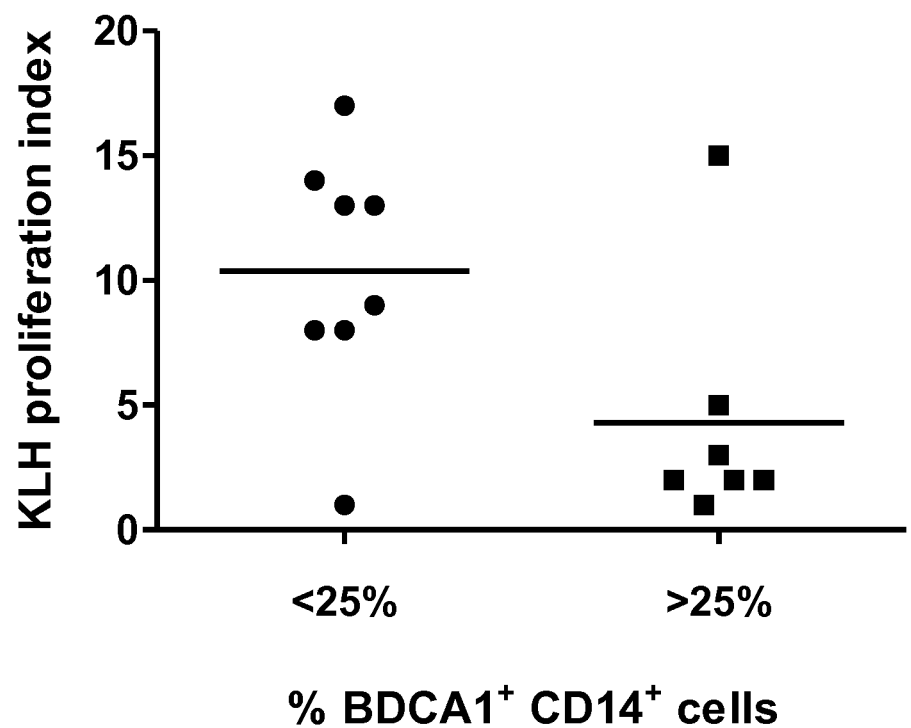
Figure 7B:
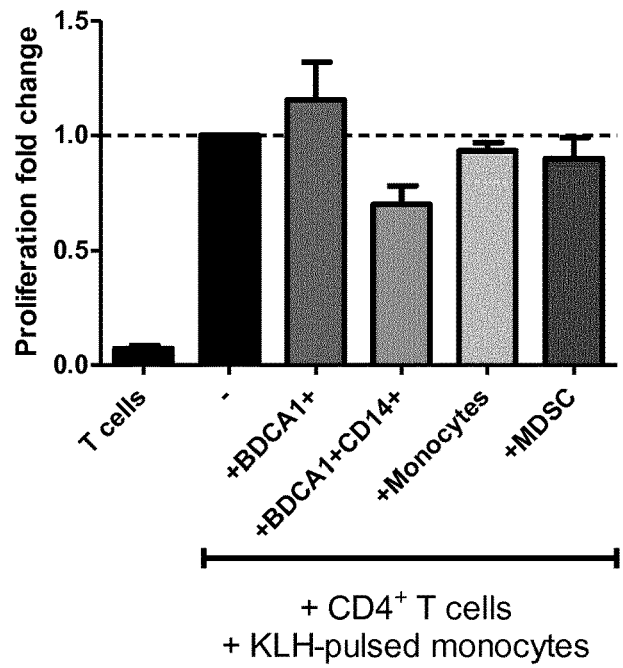
Figure 7B:
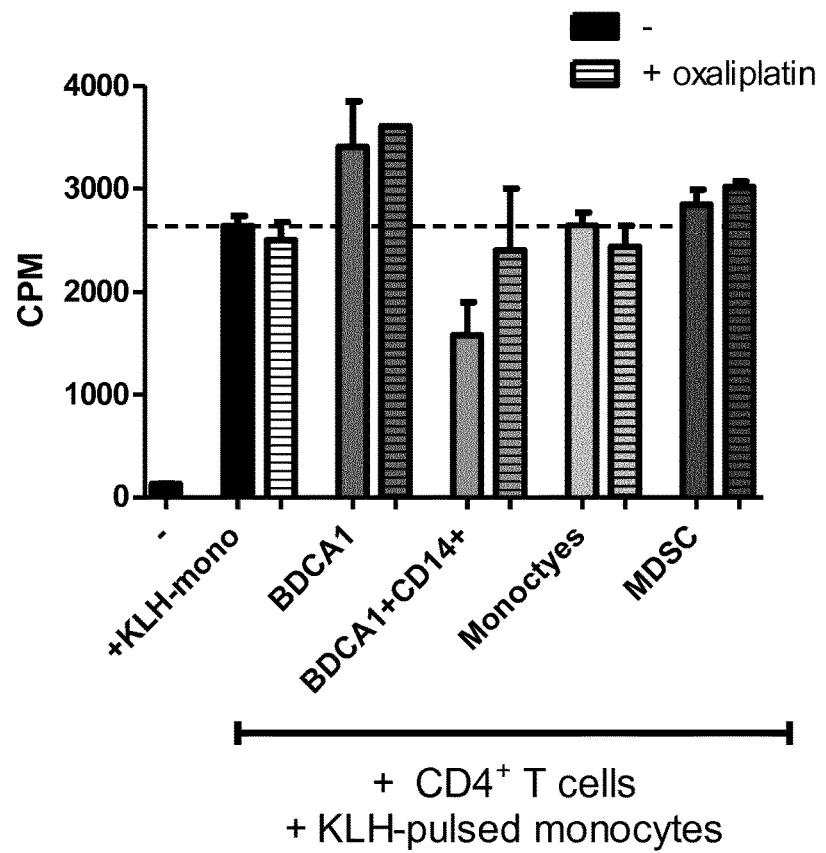
Figure 7C:
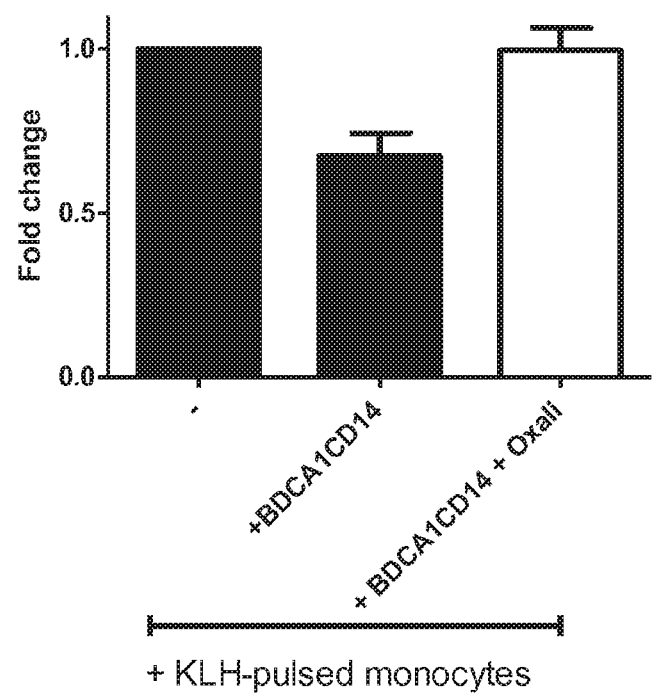
Figure 7D:
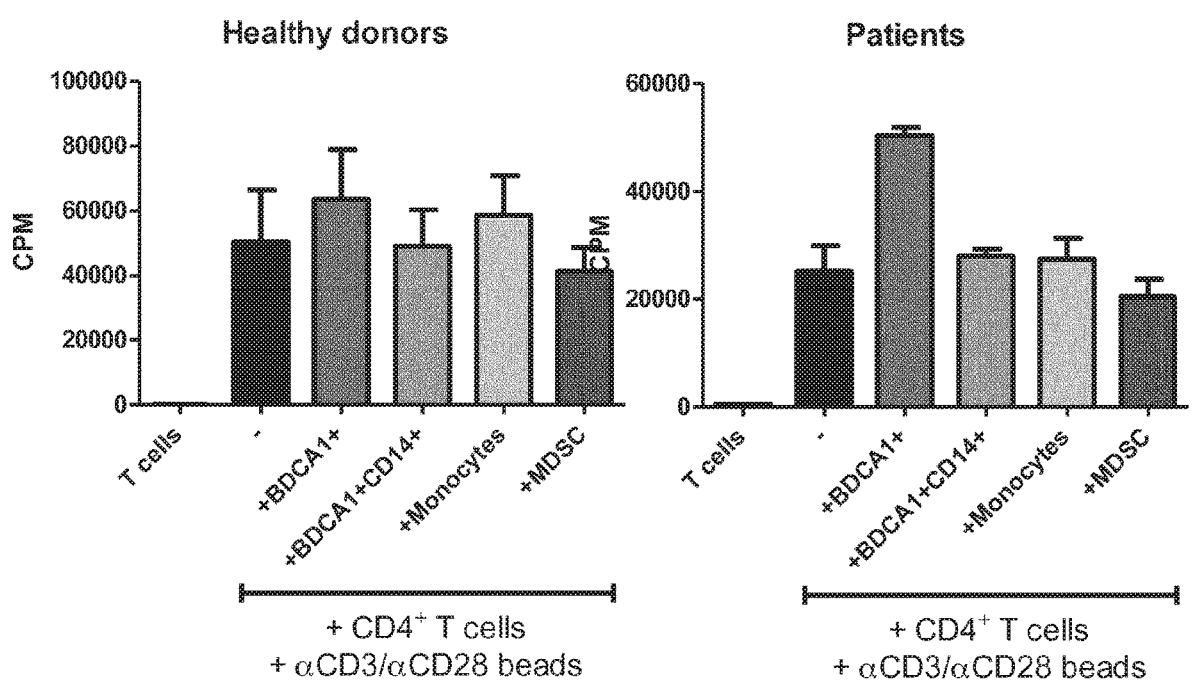

BDCA1+ CD14+ Cell Population is Associated with Lower Response Towards BDCA1+ DC-based Vaccines in Melanoma Patients In a clinical trial, BDCA1+ DC-vaccines were utilized to treat melanoma patients. BDCA1+ DCs used in these vaccines were isolated from patients' peripheral blood by means of magnetic activated cell sorting (MACS). This isolation method depends on positive selection of BDCA1-expressing cells following B lymphocyte depletion. Thus, the isolated BDCA1+ population includes both BDCA1+ DCs and BDCA1+ CD14+ cells. The percentage of the latter varied between 6% and up to 45% of the whole vaccine preparation. Based on this, patients receiving BDCA1+ DC vaccine were divided into two groups: a group that received vaccines with BDCA1+ CD14+ cellular content lower than 25% and a group that received vaccines with BDCA1+ CD14+ cellular content higher than 25%. The BDCA1+ cells used in the vaccine were loaded with the melanoma specific antigens gp-100 and tyrosinase and with keyhole limpet hemocyanin (KLH) as an immunogenic control antigen. Upon comparing the immune response towards KLH between the two groups, patients that received BDCA1+ vaccines with low content of BDCA1+ CD14+ cells displayed significantly higher KLH-specific T cell responses in comparison to patients receiving vaccines with higher than 25% of BDCA1+ CD14+ cells (FIG. 7A). This attenuated immune response may be attributed to the weak T cell stimulatory capacity of BDCA1+ CD14+ cells (FIGS. 5A-5B). However, an alternative route of dampening T cell immune responses is by actively suppressing these responses in analogy to MDSCs. To test this hypothesis, the suppressive qualities of BDCA1+ CD14+ cells, MDSCs, monocytes and BDCA1+ DCs were compared. Whereas none of these subsets were able to suppress αCD3/αCD28-induced proliferation of autologous CD4+ T cells when isolated from healthy donors, only MDSCs demonstrated T cell dampening when these cells were isolated from melanoma patients (FIG. 7D). Surprisingly, when CD4+ T cells were stimulated with KLH-loaded monocytes, only BDCA1+ CD14+ cells were able to suppress the proliferation of KLH-specific CD4+ T cells (FIG. 7B, upper panel). Interestingly, this imposed suppression is abolished in the presence of oxaliplatin, a platinum-based chemotherapeutic (FIG. 7B, lower panel). Thus, BDCA1+ CD14+ are only capable of oppressing T cell responses in antigen-specific manner, which may explain the attenuated KLH responses in melanoma patients receiving BDCA1+ DC vaccines with a high content of BDCA1+ CD14+ cells.

BDCA1+ CD14+ Cell Population can be Characterized by Specific Gating Strategy

Figure 8:
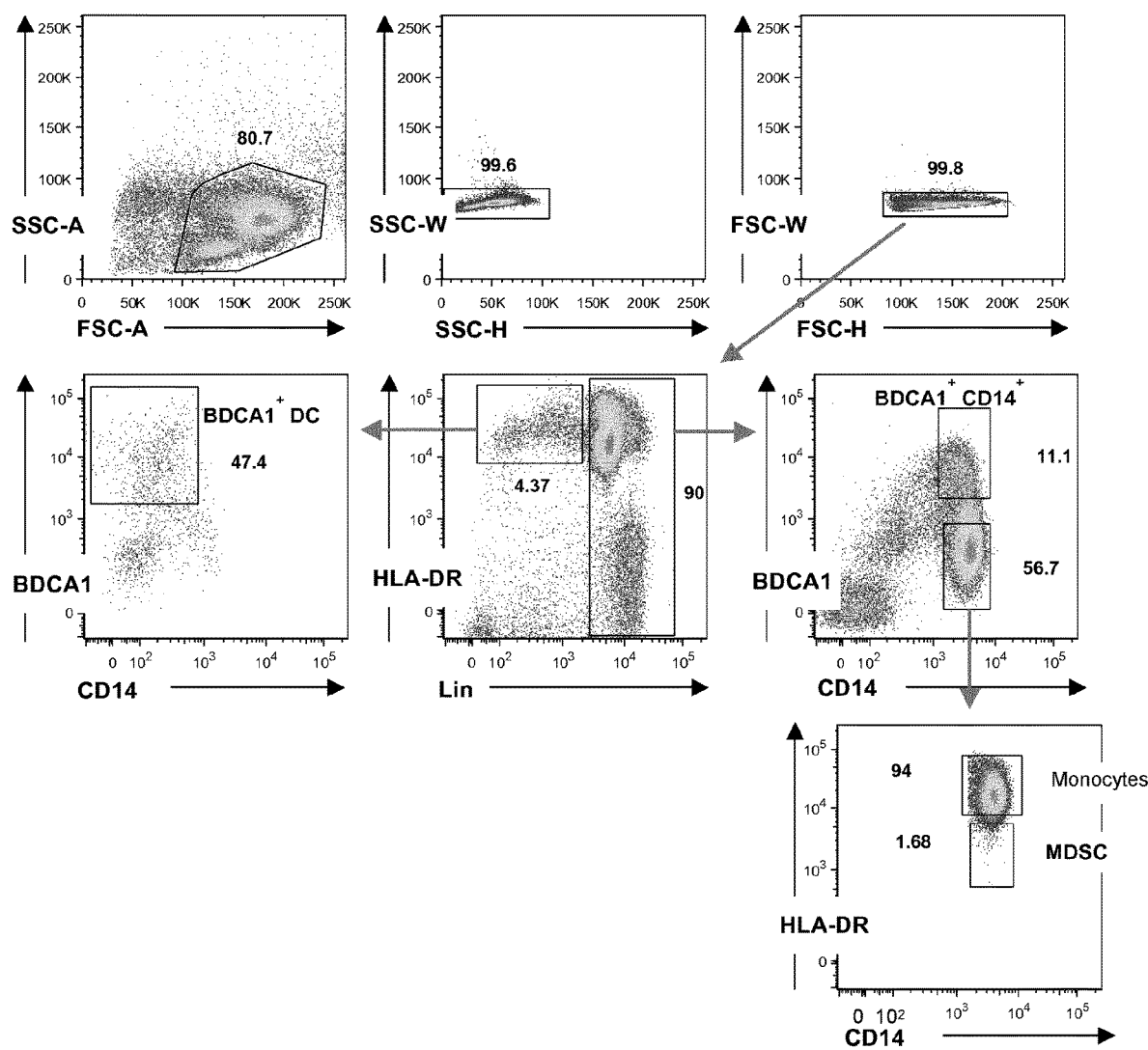
FIG. 8: A possible sorting strategy.
Figure 9:
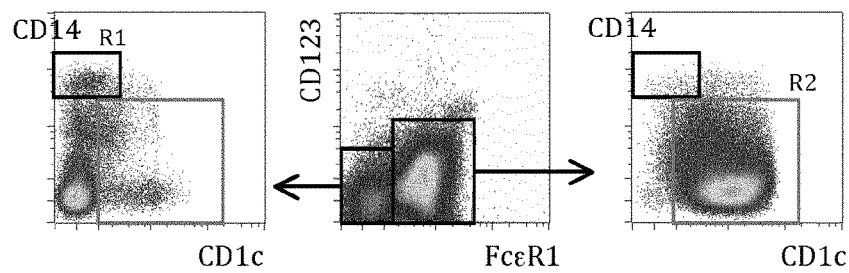
FIGS. 9-10: A composition of the invention is the "BDCA-1 enriched" cell population. According to the invention, the fraction of BDCA1+CD14+ need to be diminished to less than 25% of the total cells in order to obtain a cell population for administration to a patient suffering from cancer.
Figure 9:
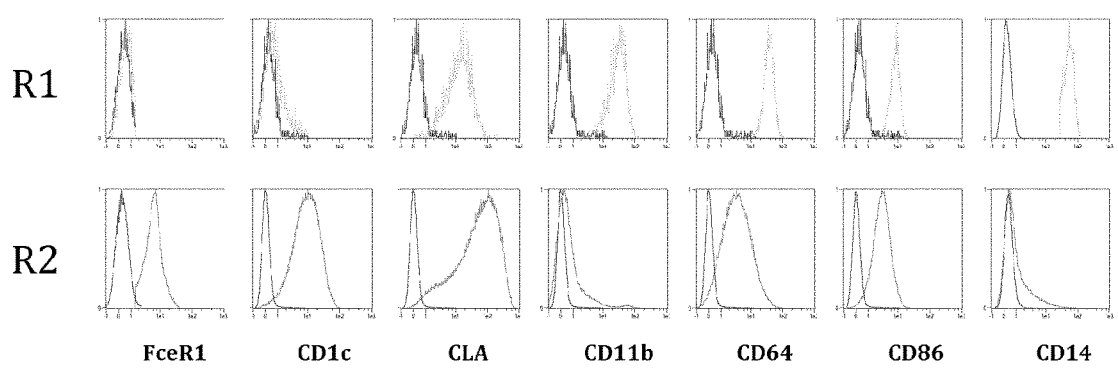
Figure 10:
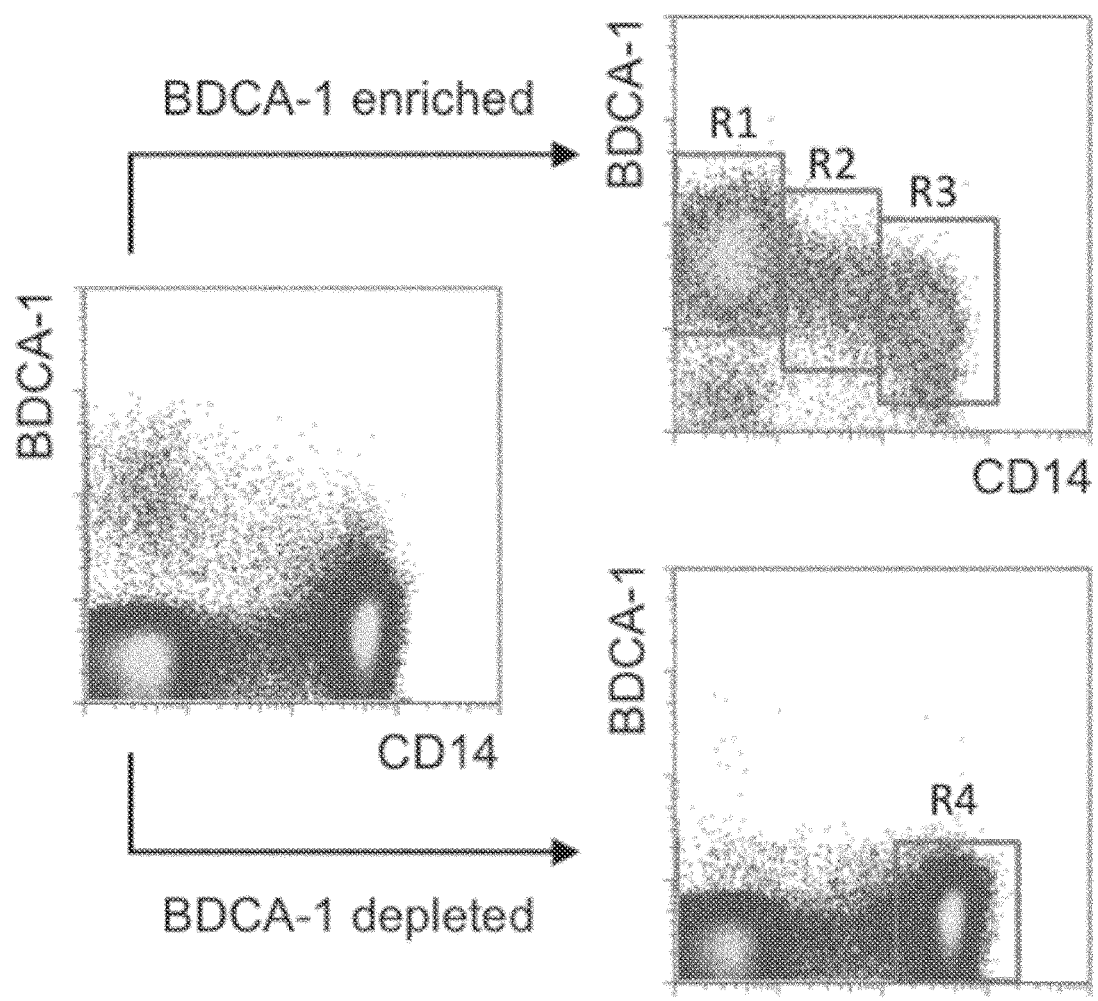

Dendritic cells from human peripheral blood are characterized by high expression level of MHC class II molecules (e.g. HLA-DR) and the lack of expression of so-called lineage markers including, for example, CD3 (for T-cells), CD14 (for monocytes), CD19 (for B-cells) and CD56 (for NK-cells). Within the HLA-DR+ Lin− cells, a subset of CD1c+CD14− blood DCs is included (FIG. 8). Lin+ cells contain CD14+ cells, which can be further divided according to the level of their CD1c expression. CD1c+ corresponds to the CD1c+CD14+ cells with the suppressive function as described above. CD1c−CD14+ cells contain two further subsets, which can be distinguished according to their expression level of HLA-DR. The first expressing high level of HLA-DR corresponds to monocytes, whereas the HLA-DR low subset corresponds to MDSC (FIG. 8). In agreement with this finding, enriched CD1c+ cells express CD14 at a different level (FIG. 9). CD1c+CD14high cells (FIG. 9, R3) express CD14 at the same level as CD14+ monocytes (FIG. 9, R4), which is in agreement with the gating strategy as shown in FIG. 8. Depending on the brightness of the CD14-fluorophore conjugate, a further CD1c+ subset can be distinguished that expresses CD14 at an intermediate level between CD1c+CD14− DC and CD1c+CD14high cells. These cells can be designated CD1c+CD14low and are included in the region R2 of the FIG. 9. CD1c+CD14low cells and CD1c+CD14high cells together constitute the CD1c+CD14+ subset as described above and shown in FIG. 8. CD1c+CD14− DCs are shown in R1.

TABLE 1

| Antibody Name | Target-UniProt Entry |
|---|---|
| ANCA | PRTN3_HUMAN |
| BDNF | BDNF_HUMAN |
| CD10 | NEP_HUMAN |
| CD10 | NEP_HUMAN |
| CD10 | NEP_HUMAN |
| CD10 | NEP_HUMAN |
| CD105 | EGLN_HUMAN |
| CD106 | VCAM1_HUMAN |
| CD11a | CD11A_HUMAN |
| CD11a | CD11A_HUMAN |
| CD11a | CD11A_HUMAN |
| CD11b | CD11B_HUMAN |
| CD11b | CD11B_HUMAN |
| CD11b | CD11B_HUMAN |
| CD11c | ITAX_HUMAN |
| CD13 | AMPN_HUMAN |
| CD13 | AMPN_HUMAN |
| CD14 | CD14_HUMAN |
| CD14 | CD14_HUMAN |

TABLE 1-continued

| Antibody Name | Target-UniProt Entry |
|---|---|
| CD14 | CD14_HUMAN |
| CD147 | BASI_HUMAN |
| CD147 | BASI_HUMAN |
| CD15 | |
| CD15 | |
| CD15 | |
| CD16 | FCG3A_HUMAN |
| CD16 | FCG3A_HUMAN |
| CD16 | FCG3A_HUMAN |
| CD162 | SELPL_HUMAN |
| CD17 | |
| CD177 | CD177_HUMAN |
| CD18 | ITB2_HUMAN |
| CD18 | ITB2_HUMAN |
| CD18 | ITB2_HUMAN |
| CD19 | CD19_HUMAN |
| CD19 | CD19_HUMAN |
| CD1a | CD1A_HUMAN |
| CD2 | CD2_HUMAN |
| CD2 | CD2_HUMAN |
| CD2 | CD2_HUMAN |
| CD20 | CD20_HUMAN |
| CD20 | CD20_HUMAN |
| CD20 | CD20_HUMAN |
| CD21 | CR2_HUMAN |
| CD22 | CD22_HUMAN |
| CD22 | CD22_HUMAN |
| CD22 | CD22_HUMAN |
| CD222 | MPRI_HUMAN |
| CD23 | FCER2_HUMAN |
| CD235a | GLPA_HUMAN |
| CD235ab | GLPB_HUMAN |
| CD24 | CD24_HUMAN |
| CD25 | IL2RA_HUMAN |
| CD25 | IL2RA_HUMAN |
| CD25 | IL2RA_HUMAN |
| CD25 | IL2RA_HUMAN |
| CD27 | CD27_HUMAN |
| CD28 | CD28_HUMAN |
| CD29 | ITB1_HUMAN |
| CD29 | ITB1_HUMAN |
| CD3 | CD3E_HUMAN |
| CD3 | CD3E_HUMAN |
| CD3 | CD3E_HUMAN |
| CD30 | TNR8_HUMAN |
| CD31 | PECA1_HUMAN |
| CD33 | CD33_HUMAN |
| CD34 | CD34_HUMAN |
| CD36 | CD36_HUMAN |
| CD37 | CD37_HUMAN |
| CD38 | CD38_HUMAN |
| CD4 | CD4_HUMAN |
| CD4 | CD4_HUMAN |
| CD4 | CD4_HUMAN |
| CD4 | CD4_HUMAN |
| CD4 | CD4_HUMAN |
| CD40 | TNR5_HUMAN |
| CD41 | ITA2B_HUMAN |
| CD41a | ITA2B_HUMAN |
| CD42b | GP1BA_HUMAN |
| CD43 | LEUK_HUMAN |
| CD43 | LEUK_HUMAN |
| CD44 | CD44_HUMAN |
| CD44 | CD44_HUMAN |
| CD45 | PTPRC_HUMAN |
| CD45 | PTPRC_HUMAN |
| CD45RA | PTPRC_HUMAN |
| CD45RA | PTPRC_HUMAN |
| CD45RA | PTPRC_HUMAN |
| CD45RB | PTPRC_HUMAN |
| CD45RO | PTPRC_HUMAN |
| CD46 | MCP_HUMAN |
| CD47 | CD47_HUMAN |
| CD48 | CD48_HUMAN |
| CD5 | CD5_HUMAN |
| CD5 | CD5_HUMAN |
| CD50 | ICAM3_HUMAN |
| CD52 | CD52_HUMAN |
| CD53 | CD53_HUMAN |
| CD53 | CD53_HUMAN |
| CD54 | ICAM1_HUMAN |
| CD54 | ICAM1_HUMAN |
| CD55 | DAF_HUMAN |
| CD55 | DAF_HUMAN |
| CD56 | NCAM1_HUMAN |
| CD56 | NCAM1_HUMAN |
| CD57 | |
| CD58 | LFA3_HUMAN |
| CD58 | LFA3_HUMAN |
| CD59 | CD59_HUMAN |
| CD59 | CD59_HUMAN |
| CD6 | CD6_HUMAN |
| CD6 | CD6_HUMAN |
| CD62L | LYAM1_HUMAN |
| CD62L | LYAM1_HUMAN |
| CD62p | LYAM3_HUMAN |
| CD63 | CD63_HUMAN |
| CD66e | CEAM5_HUMAN |
| CD69 | CD69_HUMAN |
| CD7 | CD7_HUMAN |
| CD7 | CD7_HUMAN |
| CD7 | CD7_HUMAN |
| CD7 | CD7_HUMAN |
| CD71 | TFR1_HUMAN |
| CD71 | TFR1_HUMAN |
| CD72 | CD72_HUMAN |
| CD72 | CD72_HUMAN |
| CD79a | CD79A_HUMAN |
| CD8 | CD8A_HUMAN |
| CD8 | CD8A_HUMAN |
| CD8 | CD8A_HUMAN |
| CD8 | CD8A_HUMAN |
| CD80 | CD80_HUMAN |
| CD86 | CD86_HUMAN |
| CD9 | CD9_HUMAN |
| CD9 | CD9_HUMAN |
| CD95 | TNR6_HUMAN |
| CD97 | CD97_HUMAN |
| CD98 | 4F2_HUMAN |
| CD99 | CD99_HUMAN |
| CD99R | CD99_HUMAN |
| Etoxin-1 | CCL11_HUMAN |
| FDC | |
| GM-CSF | CSF2_HUMAN |
| hIFNG | IFNG_HUMAN |
| hIFNG | IFNG_HUMAN |
| hIFNG | IFNG_HUMAN |
| hIL-10 | IL10_HUMAN |
| hIL-10 | IL10_HUMAN |
| hIL-10 | IL10_HUMAN |
| hIL-12B | IL12B_HUMAN |
| hIL-12B | IL12B_HUMAN |
| hIL-37 | IL37_HUMAN |
| hIL-37 | IL37_HUMAN |
| hIL-4 | IL4_HUMAN |
| hIL-4 | IL4_HUMAN |
| hIL-4 | IL4_HUMAN |
| hIL-8 | IL8_HUMAN |
| hIL-8 | IL8_HUMAN |
| hIL-8 | IL8_HUMAN |
| HLA I | |
| HLA-ABC | |
| HLA-DP | DPB1_HUMAN |
| HLA-DR | |
| hTNFA | TNFA_HUMAN |
| hTNFA | TNFA_HUMAN |
| hTNFA | TNFA_HUMAN |
| hTSLP | TSLP_HUMAN |
| hTSLP | TSLP_HUMAN |
| IFN gamma | IFNG_HUMAN |
| IgE | FCERA_HUMAN |
| IL-1 beta | IL1B_HUMAN |
| IL-10 | IL10_HUMAN |
| IL-15 | IL15_HUMAN |
| IL-18 | IL18_HUMAN |
| IL-6 | IL6_HUMAN |

TABLE 1-continued

| Antibody Name | Target-UniProt Entry |
| --- | --- |
| IL-7 | IL7_HUMAN |
| IL-8 | IL8_HUMAN |
| MCP-3 | CCL7_HUMAN |
| MIP-1 alpha | CCL3_HUMAN |
| MPO | PERM_HUMAN |
| pan HLA-class II | |
| TRAIL | TNF10_HUMAN |
| TRAIL | TNF10_HUMAN |
| TSLPrec | CRLF2_HUMAN |

Discussion

Immune evasion is the Achilles heel of natural immune responses and immunotherapeutics against cancer. The resourcefulness of tumors in escaping immunity is reflected by the plethora of protection mechanisms they develop. Tumors have been suggested to disrupt chemokine circuits that are pivotal for T cell attraction. Furthermore, mounting evidence indicates that tumors manipulate vascular endothelium to form a physical barrier in the face of tumor-reactive T cells and to actively suppress these cells. Once T cells manage to transmigrate through the endothelial barrier, these T cells have to negotiate a hostile immunosuppressive tumor stroma before encountering tumor cells. Indeed, tumors recruit and promote the expansion of immunosuppressive leukocyte populations like Treg cells, MDSCs and M2 macrophages. In this study, the inventors introduce a new member to the immunosuppressive leukocyte family; BDCA1$^+$ CD14$^+$ cells. Although the inventors mainly characterized this new population in peripheral blood, they were able to trace this population in ascites fluid of ovarian cancer patients. Similar to MDSCs, this population is significantly elevated in peripheral blood of melanoma patients, supporting the notion that tumors promote the accumulation of suppressive elements in peripheral tissues. A common feature between MDSCs and BDCA1$^+$ CD14$^+$ cells is the expression of CD14, which may imply a joint origin. However, these two suppressive populations vary in the mode of suppression. Whereas MDSCs universally suppress the proliferation of bystander T cells, BDCA1$^+$ CD14$^+$ cells only suppress T cells in an antigen-specific manner. This difference may be linked to the expression levels of HLA-DR important for antigen presentation to CD4$^+$ T cells. Whereas MDSCs are by definition HLA-DR$^{low}$, BDCA1$^+$ CD14$^+$ cells express HLA-DR at high levels equivalent to expression by BDCA1$^+$ DCs. In line with this, Nagaraj and colleagues found that in a special cancer mouse model (MC38) CD4$^+$ T cell tolerance was observed and attributed to a special type of MDSCs expressing substantial levels of MHC-II. Based on this, BDCA1$^+$ CD14$^+$ cells could be categorized as a MHC-II$^{hi}$ subset of MDSCs. However, the big differences in RNA expression profiles between these two subsets argue against such classifying BDCA1$^+$ CD14$^+$ cells as MDSCs. Transcriptome analysis also revealed a possible relation between BDCA1$^+$ CD14$^+$ cells and macrophages as demonstrated by the expression of genes that are pivotal for macrophage differentiation in mice. Nevertheless, CSF1R was also reported to be highly expressed by inflammatory DCs (infDCs) in both mice and humans. Moreover, the fact that macrophages are by definition tissue-resident cells whereas BDCA1$^+$ CD14$^+$ cells are found in both circulation and tissues highlights another discrepancy between the two cell subsets and argues against classifying them in the same group. Yet the potential similarities between BDCA1$^+$ CD14$^+$ cells and macrophages urges for further delineation of the link between the two. CD14 expression is not restricted to monocytes as DCs in certain compartments or under certain conditions do express CD14. Indeed, steady-state human dermis harbors a CD14$^+$ subset of dermal DCs (DDCs). Similar to the BDCA1$^+$ CD14$^+$ population, CD14$^+$ DDCs express BDCA1 allowing their distinction from dermal macrophages. This phenotypical resemblance between these two subsets is further supported by overlapping functional qualities. In analogy to BDCA1$^+$ CD14$^+$ cells, CD14$^+$ DDCs were demonstrated to express low levels of costimulatory molecules rendering them poor inducers of nave T cell proliferation.

Furthermore, CD14$^+$ DDCs have been implicated in the induction of immune tolerance by promoting the development of Treg cells. The shared traits between BDCA1$^+$ CD14$^+$ cells and CD14$^+$ DDCs strongly suggest a link between the two populations, an issue that requires further investigation. In addition to CD14$^+$ DDCs, upregulated CD14 expression by DCs is also observed following their treatment with immunomodulatory reagents like vitamin D, dexamethasone and IL-10. The common feature among all these CD14$^+$ DCs is the low expression of costimulatory molecules, poor induction of T cell responses and promotion of immune tolerance. This strongly postulates that BDCA1$^+$ CD14$^+$ blood population may be indeed a circulating inhibitory DC subset, a notion that is corroborated by the close RNA expression profile between BDCA1$^+$ CD14$^+$ cells and BDCA1$^+$ DCs.

The tumor-associated immunosuppressive machinery functions in part through immune inhibitory molecules that mitigate tumor-specific immune responses through ligating their cognate receptors on immune cells rendering them dysfunctional. Among these inhibitory routes, also referred to as check-points, is the PD-1/PD-L1 pathway. PD-1 is a member of the CD28 family that is expressed by activated T and B cells and possesses two ligands PD-L1 and PD-L2, which have a variable expression on DCs, macrophages and T cells. Triggering of PD-1 by one of its ligands during T cell receptor signaling can block T cell proliferation, cytokine production and cytolytic activity and impair T cell survival. These inhibitory effects are attributed to the immunoreceptor tyrosine-based inhibitory motif (ITIM) and immunoreceptor tyrosine-based switch motif (ITSM) within the intracellular domain of PD-1[45]. The inhibitory effects of PD-L1/PD-1 pathway can be hijacked by tumors to evade anti-tumor immune responses. PD-L1 expression has been confirmed on many tumors including glioblastoma and melanoma as well as cancers of the head and neck, lung, ovary, colon, stomach, kidney and breast. High expression PD-L1 levels by tumor cells, tumor infiltrating lymphocytes or both associated with aggressive tumor behavior, poor prognosis and elevated risk of mortality. Furthermore, the inventors described here that the BDCA1$^+$ CD14$^+$ population is characterized by elevated expression of PD-L1, which is partially responsible for its poor T cell stimulatory capacity. Therefore, the PD-L1/PD-1 check-point is a very interesting target to neutralize the tumor immunosuppressive machinery. Indeed, targeting this pathway by blocking antibodies against PD-1 or PD-L1 not only proved tolerable, but showed durable anti-tumor responses in up to 28% of all treated patients. Another anti-PD-1 mAb developed by Merck (MK-3475) has been recently reported to achieve a clinical response rate of up to 50% of the treated advanced melanoma patients. Thus, check-point inhibitors have a promising future in cancer immunotherapy, especially when combined with other forms of immunotherapy like DC vaccines.

Taken together, the inventors found a novel cellular subset by which tumors maintain a systemic state of immune suppression, prohibiting any active anti-tumor immune responses. The inhibitory functions of this $BDCA1^+$ $CD14^+$ population makes it a target for cancer immunotherapy.

The invention claimed is:

1. A cell population for use in treating cancer in a patient, comprising:
   CD1c+/CD19− myeloid dendritic cells, wherein less than or equal to 25% of the CD1c+/CD19− dendritic cells are CD1c+/CD19−/CD14+ cells; and
   cells that are CD304+(BDCA-4+) plasmacytoid dendritic cells.

2. The cell population of claim 1, wherein at least 50% of the cells are loaded with a tumor antigen or a tumor peptide.

3. The cell population of claim 1, wherein the cells are purified from blood of the patient to be treated for cancer.

4. The cell population of claim 1, wherein the cancer is a solid cancer or a blood cancer.

5. The cell population of claim 4, wherein the cancer is chronic myeloid leukemia.

6. The cell population of claim 4, wherein the cancer is melanoma or prostate cancer.

7. The cell population of claim 1, wherein when the cell population includes less than or equal to 25% of the CD1c+/CD19− dendritic cells being CD1c+/CD19−/CD14+ cells the cell population has a reduced immunosuppressive activity compared to a cell population wherein more than 25% of the CD1c+/CD19− dendritic cells are CD1c+/CD19−/CD14+ cells.

* * * * *